(12) United States Patent
Love et al.

(10) Patent No.: US 7,105,550 B2
(45) Date of Patent: Sep. 12, 2006

(54) 2,4-DISUBSTITUTED THIAZOLYL DERIVATIVES

(76) Inventors: Christopher Love, 2100 Deurne, Janssen Pharmaceutica N.V., Turnhoutseweg 30, Beerse, 2340 (BE); Jean Pierre Frans Van Wauwe, 2340 Beerse, Janssen Pharmaceutica N.V., Tumhoutseweg 30, Beerse, 2340 (BE); Marc De Brabander, 2980 Zoersel, Janssen Pharmaceutica N.V., Tumhoutseweg 30, Beerse, 2340 (BE); Ludwig Cooymans, 2340 Beerse, Janssen Pharmaceutica N.V., Tumhoutseweg 30, Beerse, 2340 (BE); Nele Vandermaesen, 2491 Olmen, Janssen Pharmaceutica N.V., Tumhoutseweg 30, Beerse, 2340 (BE); Ludo Edmond Josephine Kennis, 2300 Tumhout, Janssen Pharmaceutica N.V., Tumhoutseweg 30, Beerse, 2340 (BE)

( * ) Notice: Subject to any disclaimer, the term of this patent is extended or adjusted under 35 U.S.C. 154(b) by 174 days.

(21) Appl. No.: 10/220,350

(22) PCT Filed: Feb. 20, 2001

(86) PCT No.: PCT/EP01/01841

§ 371 (c)(1),
(2), (4) Date: Aug. 29, 2002

(87) PCT Pub. No.: WO01/64674

PCT Pub. Date: Sep. 7, 2001

(65) Prior Publication Data

US 2003/0203897 A1    Oct. 30, 2003

(30) Foreign Application Priority Data

Mar. 1, 2000   (EP) .................................. 00200733

(51) Int. Cl.
*A61K 31/41* (2006.01)
*A61K 31/425* (2006.01)
*A61K 31/415* (2006.01)

(52) U.S. Cl. .................. 514/365; 514/367; 514/368; 514/388; 514/387; 514/394; 514/393; 514/396

(58) Field of Classification Search ................ 514/368, 514/367, 365, 394, 387, 388, 393, 396
See application file for complete search history.

(56) References Cited

U.S. PATENT DOCUMENTS 3,459,731 A    8/1969   Gramera et al.

FOREIGN PATENT DOCUMENTS

DE    3406329 A1    8/1985

| DE | 4029771 A1 | 3/1992 |
|---|---|---|
| GB | 2022085 A | 12/1979 |
| JP | 55-133366 A | 10/1980 |
| JP | 62-067022 A | 3/1987 |
| JP | 62-067023 A | 3/1987 |
| JP | 62-108859 A | 5/1987 |
| JP | 04-154773 A | 5/1992 |
| WO | WO 92/16527 A1 | 1/1992 |
| WO | WO 97/03073 A1 | 1/1997 |
| WO | WO 97/18839 A1 | 5/1997 |
| WO | WO 99/21555 A2 | 5/1999 |

(Continued)

OTHER PUBLICATIONS

Beers, M., The Merck Manual of Diagnosis and Therapy (17th ED) (1999), p. 302-305 and 416-417.*

(Continued)

*Primary Examiner*—San-Ming Hui

(57) ABSTRACT

This invention concerns the use of a compound of formula (I')

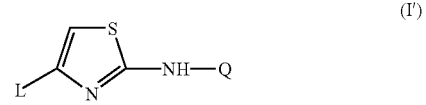

(I')

a N-oxide, pharmaceutically acceptable addition salt, quaternary amine and stereochemically isomeric form thereof, wherein Q is optionally substituted $C_{3-6}$cycloalkyl, phenyl, naphthyl, pyridyl, pyrimidinyl, pyrazinyl, pyridazinyl, benzthiazolyl, benzoxazolyl, benzimidazolyl, indazolyl, or imidazopyridyl; or Q is a radical of formula

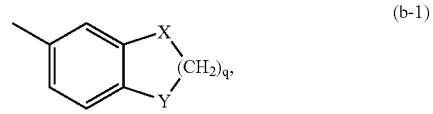

(b-1)

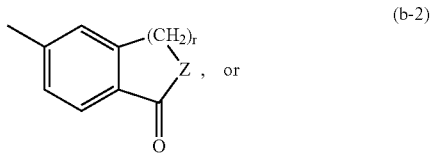

(b-2)

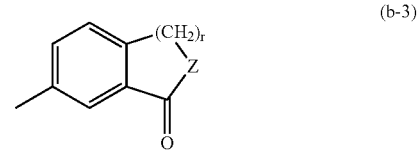

(b-3)

wherein X and Y each independently are O, $NR^3$, $CH_2$ or S, with $R^3$ being hydrogen or $C_{1-4}$alkyl; q is 1 to 4; Z is O or $NR^4$ with $R^4$ being hydrogen or $C_{1-4}$alkyl; r is 1 to 3; L is optionally substituted phenyl or L is Het with Het being an optionally substituted five- or six-membered heterocyclic ring or an optionally substituted bicyclic heterocyclic ring; for the manufacture of a medicament for the prevention or the treatment of diseases mediated through cytokines.

7 Claims, No Drawings

FOREIGN PATENT DOCUMENTS

| WO | WO 99/32466 A1 | 7/1999 |
|---|---|---|
| WO | WO 99/64418 A1 | 12/1999 |
| WO | WO 00/17175 A1 | 3/2000 |
| WO | WO 00/33837 A2 | 6/2000 |

OTHER PUBLICATIONS

Chemical Abstracts, vol. 82, No. 5, Abstract No. 31289, 1975, XP-002151288.

Chemical Abstracts, vol. 83, No. 23, Abstract No. 193158, 1975, XP-002143922.

Chemical Abstracts, vol. 88, No. 15, Abstract No. 105204, 1978, XP-002151291.

Chemical Abstracts, vol. 89, No. 23, Abstract No. 197384, 1978, XP-002170057.

Chemical Abstracts, vol. 90, No. 9, Abstract No. 72098, 1979, XP-002151289.

Chemical Abstracts, vol. 94, No. 7, Abstract No. 47195, 1981, XP-002151292.

Chemical Abstracts, vol. 94, No. 17, Abstract No. 139797, 1981.

Chemical Abstracts, vol. 103, No. 7, Abstract No. 53986, 1985, XP002151290.

Chemical Abstracts, vol. 107, No. 8, Abstract No. 64874, 1987.

Chemical Abstracts, vol. 107, No. 8, Abstract No. 64875, 1987.

Chemical Abstracts, vol. 107, No. 21, Abstract No. 197776, 1987.

Chemical Abstracts, vol. 108, No. 25, Abstract No. 221648, 1988, XP002143924.

Chemical Abstracts, vol. 111, No. 3, Abstract No. 23457, 1989, XP-002143923.

Chemical Abstracts, vol. 117, No. 21, Abstract No. 212486, 1992.

Database Chemcats "Online" Accession No. 1998-629695; XP-002170058.

Batta A.K. et al., "Syntheses of 4-(2'-Thienyl)—And 4-(2'-Furyl)-Thiazoles." *Current Science*, Fortnightly Journal of Research, 1970, pp. 417-418, vol. 39, No. 18.

Taurins A. et al., "Synthesis of Pyridyl-and Quinolyl-Substituted 2-Aminothiazoles (I)." *J. Heterocyclic Chem.*, 1970, pp. 1137-1141, vol. 7, No. 5.

Sawhney S.N. et al., "Benzothiazole Derivatives: Part III. Synthesis and Antiinflammatory Activity of Some 2-(2-Amino-4-thiazolyl)-benzolthiazoles." *J. Indian Chem. Soc.*, 1974, pp. 566-568, vol. 51, No. 5.

Sawhney S.N. et al., "Synthesis and Antiinflammatory Activity of some 6-[2-Amino-(and substituted amino)-4-thiazolyl] benzothiazoles." *J. Indian Chem.Soc.*, 1975, pp. 561-562, vol. LII, No. 6.

Westphal G.V. et al., "Synthesis of pyridylthiazoles." *P. Prakt. Chem.*, 1976, pp. 857-877, vol. 318, No. 5 (English Abstract provided).

Mandal A.K. et. "Studies on Dissociation Constants of Substituted Salicylic Acids in Ethanol-Water Mixtures by Conductometric Method." *J. Indian Chem.* 1977, pp. 728-730, vol. 15A.

Singh S.P. et al., "TLC Seperation of Some Isomeric 2-and 6-[2-Amino (and substituted amino)-4-thiazolyl] Benzothiazoles." *Fresenius Z. Anal. Chem.*, 1977, p. 288, vol. 285.

Thakar K.A., "Synthesis of 2-(Substituted Anilino) 4-(Substituted Phenyl) thiazoles." *J. Pharm. Sci.*, 1978, pp. 587-589, vol. 67, No. 4.

Arya V.P. et al., "Isothiazoles: Part VIII* —Synthesis & Biological Activity of 4-(2-Amino-4-thiazolyl)isothiazoles." *Indian J. Chem.*, 1978, pp. 402-404, vol. 16B, No. 5.

Patil V.H. et al., "Synthesis of 2-Arylamino-4-[2'-(p-acetamido-benzenesulphonamido)-6'-benzothiazolyl] thiazoles & 2-Arylamino-4-(2'-sulphanilamido-6'-benzothiazolyl) thiazoles." *Indian J. Chem.*, 1979, pp. 519-521, vol. 17B, No. 2.

Upadhya K.G. et al., "Synthesis d Antiinflammatory Activity of 3-Substituted 4-(4'-Thiazolyl)-Sydnones." *Arch. Pharm.* (*Weinheim*), 1980, pp. 684-688, vol. 313.

Metri J. et al., "Synthesis of New, Sulphamylanilino Substituted Thiazoles of Potential Biological Activity," *Egypt J. Chem.*. 1982, pp. 187-189, vol. 25, No. 2.

Kapoor R.P. et al., "Synthesis of Thiazolylchromones as Potential CNS Agents." *Indian J. Chem.*, 1984, pp. 390-392, vol. 23B, No. 1.

Hanmantgad S.S. et al., "Biomimetic thiazolyt coumarins." *Natl. Acad. Sci. Letters*, 1984, pp. 77-78, vol. 7, No. 3.

Nogradi M. "Dimethyl-β-Cyclodextrin." *Drugs of the Future*, 1984, pp. 577-578, vol. 9, No. 8.

English Abstract of DE3406329, "New 2 (1H)-pyridone derivs. With positive inotropic activity—prepd. e.g. by reaction of 1,3-dioxo cpds. with acetamide or acetonitrile cpds," 1985.

Khadse B.G. et al., "Synthesis & Antitubercular Activity of 4-(5-Nitro-2-furyl/2-pyrazinyl/1-adamantyl)-2-(alkyl/aryl/arylamino) thiazoles." *Indian J. Chem.*, 1987, pp. 856-860, vol. 26B, No. 9.

Sastry C.V.R. et al., "Synthesis & Biological Activity of Some New 6-Isothiocyanato-6, 6-N-[N,N-Bis(methoxycarbonyl) guanidine]-, & 6-(2-Aryl/2-arylaminothiazol-4-yl)-2H-1,4-benzoxazin-3(4H)-ones." *J. Indian Chem.*, 1987, pp. 662-685, vol. 26B.

Sawhney S.N., "Synthesis of some 2-Heterocyclylphenothiazines as Potential Anti-inflammatory Agents." *J. Indian Chem. Soc.*, 1988, pp. 643-647, vol. LXV.

Avetisyan A.A. et al., "Synthesis and activity of unsaturated γ-lactones with thiazoles fragments on the growth and development of vegetable crops." *Biol. Zh. Am.* 1989, pp. 956-959, vol. 42, Nos. 9-10 (English Abstract provided).

Avetisyan A.A. et al., "Unsaturated lactones. Synthesis of δ-lactones with heterocyclic substituents." *Am. Khim. Zh.*, 1989, pp. 657-659, vol. 42, No. 10 (English Abstract provided).

English Abstract of DE4029771, "New N-hetero-aryl-2-nitroaniline derives.—useful as insecticides, acaricides and nematocides." 1992.

English Abstract of WO92/16527, "New 2-substd. Pyridine derives. Useful as agricultural-horticultural bactericides—e.g. 2-(4-chlorobenzyl)-4-(6-methyl-2pyridyl) thiazole." 1992.

Zohdi H. F. et al., "Reactions with Hydrazonoyl Halides, Part 20, Synthesis of New Unsymmetrical Azines, Dihydro-1,3,4-thiadiazoles and 5-Arylazothiazoles." *J. Chem Research (S)*, 1998, pp. 742-743.

Singh S.P. et al., "A Convenient Synthesis Of 4-(2-Furyl)-2-Substituted Thiazoles Utilising [Hydroxy (Tosyloxy) Iodo] Benzene." *Synthethic Communications*, 1998, pp. 2371-2378, vol. 28, No. 13.

International Search Report, PCT/EP01/01841, dated May 7, 2001 which relates to U.S. Appl. No. 10/220,350.

\* cited by examiner

2,4-DISUBSTITUTED THIAZOLYL DERIVATIVES

CROSS REFERENCE TO RELATED APPLICATIONS

This application is a National Stage application under 35 U.S.C. §371 of PCT/EP01/01841 filed Feb. 20, 2001, which claims priority from EP 00.200.733.4, filed Mar. 1, 2000.

The present invention is concerned with 2,4-disubstituted thiazolyl derivatives having proinflammatory cytokine production inhibiting properties and adenosine $A_3$ receptor blocking properties. The invention further relates to methods for their preparation and pharmaceutical compositions comprising them. The invention also relates to the use of 2,4-disubstituted thiazolyl derivatives for the manufacture of a medicament for the prevention or the treatment of warm-blooded animals suffering from diseases mediated through cytokines or diseases mediated through activation of the adenosine $A_3$ receptor.

JP 41020220 describes 2-(2-substituted-4-thiazolyl)benzimidazole derivatives as anthelmintics and insecticides.

J. Prakt. Chem., 1976, 318(5), 875–877 describes the synthesis of pyridyl thiazoles.

J. Indian. Chem. Soc., 1974, 51(5), 566–568 describes the synthesis and anti-inflammatory activity of some 2-(2-amino-4-thiazolyl)benzothiazoles.

Fresenius'Z. Anal. Chem., 1977, 288(4), 285 describes the TLC separation of some 2- and 6-[2-amino(and substituted amino)-4-thiazolyl]benzothiazoles.

Indian J. Chem., 1978, 16B(5), 402–404 describes the synthesis and analgesic, anti-inflammatory activity of 4-(2-amino-4-thiazolyl)isothiazoles.

WO 97/03073 describes the preparation of thiazolyl triazolothiazoles as anti-ulcer agents and gastric acid secretion inhibitors.

Indian J. Chem., 1979, 17B(5), 519–521 describes the synthesis of 2-amino-6-benzothiazolyl-2-arylaminothiazoles.

Indian J. Chem., 1987, 26B(9), 856–860 describes the synthesis and antituberculosis activity of 2-pyrazinyl-2-arylaminothiazoles.

WO 92/16527 describes the synthesis of 6-methyl-2-pyridyl-2-arylaminothiazoles as agrochemical and horticultural fungicides.

J. Heterocycl. Chem., 1970, 7(5), 1137–1141 describes the synthesis of pyridyl substituted 2-aminothiazoles.

DE 3406329 describes the synthesis of 2-pyridinon-2-arylaminothiazole derivatives as inotropic agents.

J. Chem. Res., Synop., 1998, 12, 742–743, 3329–3347 describes 2-arylamino thiazole derivatives as intermediates to synthesize 5-arylazothiazoles.

Synth. Commun., 1998, 28(13), 2371–2378 describes the synthesis of 4-(2-furyl)-2-substituted thiazoles utilizing [hydroxy(tosyloxy)iodo]benzene.

Curr. Sci., 1970, 39(18), 417 describes the synthesis of 4-(2'-thienyl) and 4-(2'-furyl)-thiazoles.

DE 4029771 describes the synthesis of N-heteroaryl-2-nitroanilines as pesticides.

WO 99/32466 describes the preparation of substituted benzenesulfonamide derivatives as antagonists of the neuropeptide NPY receptor subtype Y5.

Egypt. J. Chem., 1983, 25(2), 187–189 describes the synthesis of sulfamylanilino substituted thiazoles showing bactericidal and fungicidal activity.

Am. Khim. Zh., 1989, 42(10), 657–659 describes the synthesis of 8-lactones with heterocyclic substituents.

Indian J. Chem., Sect. B, 1984, 23B(4), 390–392 describes the synthesis of thiazolylchromones as potential central nervous system agents.

Biol. Zh. Am., 1989, 42(9–10), 956–959 describes the synthesis and activity of unsaturated γ-lactones with thiazole fragments on the growth and development of vegetable crops.

WO 99/21555 relates to pyridyl substituted thiazolyl compounds having adenosine $A_3$ receptor antagonistic activity.

WO 99/64418 concerns aryl pyridinyl thiazoles exhibiting inhibition of the human adenosine $A_3$ receptor activation and of tumor necrosis factor alpha production.

The compounds of the present invention are distinguishable from the prior art because of their structure, pharmacological activity or potency.

The present invention relates to the use of a compound for the manufacture of a medicament for the prevention or the treatment of diseases mediated through cytokines, wherein the compound is a compound of formula

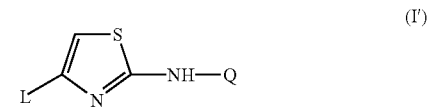

(I')

a N-oxide, a pharmaceutically acceptable addition salt, a quaternary amine and a stereochemically isomeric form thereof, wherein Q is $C_{3-6}$cycloalkyl, phenyl, naphthyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo-$C_{1-6}$alkylcarbonyl; $C_{1-4}$alkyl-S(=O)$_n$— or $R^1$HN—S(=O)$_n$—;

or

Q is a radical of formula

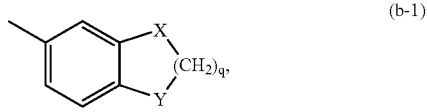

(b-1)

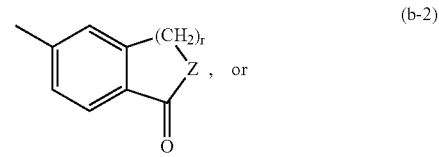

(b-2)

or

wherein X and Y each independently are O, NR³, CH₂ or S, with R³ being hydrogen or $C_{1-4}$alkyl;

q is an integer with value 1 to 4;

Z is O or NR⁴ with R⁴ being hydrogen or $C_{1-4}$alkyl;

r is an integer with value 1 to 3;

n is an integer with value 1 or 2;

R¹ represents hydrogen, or a radical of formula

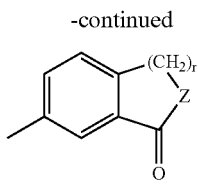

with A being O, S or a bivalent radical of formula —CR$^{2a}$=N— with CR$^{2a}$ attached to N of formula (a-1); and R$^{2a}$ being hydrogen, $C_{1-6}$alkyl or $C_{1-6}$alkyloxy;

L is phenyl, optionally substituted with up to 4 substituents each independently being selected from halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, H₂N—C(=O)—NH— or mono- or di($C_{1-4}$alkyl)amino-C(=O)—NH—; or L is Het;

Het is (i) an optionally substituted five- or six-membered heterocyclic ring containing at least two double bonds and containing 1, 2, 3 or 4 heteroatoms each independently being selected where possible from N, S or O;

(ii) an optionally substituted five- or six-membered heterocyclic ring containing at least two double bonds and containing 1, 2, 3 or 4 heteroatoms each independently being selected where possible from N, S or O and being fused through 2 carbon atoms, 2 nitrogen atoms or 1 carbon and 1 nitrogen atom with another optionally substituted five- or six-membered ring, which contains, apart from the atoms in common with the first ring, only carbon atoms; the latter ring may be unsaturated, partially unsaturated or saturated;

(iii) an optionally substituted five- or six-membered heterocyclic ring containing at least two double bonds and at least one heteroatom and being fused through 2 carbon atoms, 2 nitrogen atoms or 1 carbon and 1 nitrogen atom with another optionally substituted five- or six-membered heterocyclic ring, which contains, apart from the atoms in common with the first ring, at least one heteroatom; the latter ring may be unsaturated, partially unsaturated or saturated; said bicyclic ring system contains in total from 2 up to 6 heteroatoms, each independently being selected where possible from N, S or O;

wherein Het being a monocyclic ring system may optionally be substituted with up to 4 substituents, and wherein Het being a bicyclic ring system may optionally be substituted with up to 6 substituents, said substituents each independently being selected from halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$ alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, H₂N—C(=O)—NH— or mono- or di($C_{1-4}$ alkyl)amino-C(=O)—NH—;

aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino.

The present invention also relates to a compound of formula

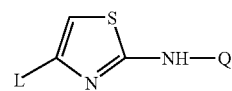

a N-oxide, a pharmaceutically acceptable addition salt, a quaternary amine and a stereochemically isomeric form thereof, wherein Q is $C_{3-6}$cycloalkyl, phenyl, naphthyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhaloC,alkyl; polyhalo-$C_{1-6}$ alkyloxy; polyhalo-$C_{1-6}$alkylcarbonyl; $C_{1-4}$alkyl-S(=O)$_n$— or R¹HN—S(=O)$_n$—;

or

Q is a radical of formula

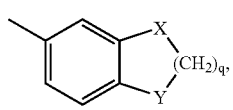

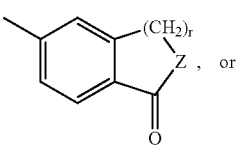

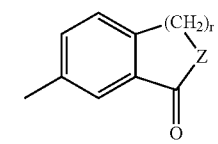

wherein X and Y each independently are O, NR³, CH₂ or S, with R³ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3;
n is an integer with value 1 or 2;
$R^1$ represents hydrogen, or a radical of formula

(a-1)

with A being O, S or a bivalent radical of formula $-CR^{2a}=N-$ with $CR^{2a}$ attached to N of formula (a-1); and
$R^{2a}$ being hydrogen, $C_{1-6}$alkyl or $C_{1-6}$alkyloxy;

L is 3-halophenyl, optionally substituted with 1, 2 or 3 substituents each independently being selected from halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—; or
L is Het;

Het is (i) an optionally substituted five- or six-membered heterocyclic ring containing at least two double bonds and containing 1, 2, 3 or 4 heteroatoms each independently being selected where possible from N, S or O;
(ii) an optionally substituted five- or six-membered heterocyclic ring containing at least two double bonds and containing 1, 2, 3 or 4 heteroatoms each independently being selected where possible from N, S or O and being fused through 2 carbon atoms, 2 nitrogen atoms or 1 carbon and 1 nitrogen atom with another optionally substituted five- or six-membered ring, which, contains, apart from the atoms in common with the first ring, only carbon atoms; the latter ring may be unsaturated, partially unsaturated or saturated;
(iii) an optionally substituted five- or six-membered heterocyclic ring containing at least two double bonds and at least one heteroatom and being fused through 2 carbon atoms, 2 nitrogen atoms or 1 carbon and 1 nitrogen atom with another optionally substituted five- or six-membered heterocyclic ring, which contains, apart from the atoms in common with the first ring, at least one heteroatom; the latter ring may be unsaturated, partially unsaturated or saturated; said bicyclic ring system contains in total from 2 up to 6 heteroatoms, each independently being selected where possible from N,S or O;
wherein Het being a monocyclic ring system may optionally be substituted with up to 4 substituents, and wherein Het being a bicyclic ring system may optionally be substituted with up to 6 substituents, said substituents each independently being selected from halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$ alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—;
aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino.

provided that
Het is other than optionally substituted isothiazolyl, 2-pyridyl, benzthiazolyl, benzoxazinyl and benzoxazinonyl;
when Q is phenyl substituted with hydroxy or $C_{1-6}$alkyloxy and carboxy or $C_{1-6}$alkyloxycarbonyl then Het is other than 3-pyridyl or 4-pyridyl;
when Q is phenyl then Het is other than 2-thienyl, 2-furanyl, 5-bromo-2-benzofuranyl, 1,2-dihydro-6-methyl-2-oxo-3-cyano-5-pyridyl, 2-benzofuranyl, 5-chloro-2-benzimidazolyl, 2-benzimidazolyl, 3-pyridyl, 4-pyridyl, 6-methyl-thiazolo [3,2-b] [1,2,4]triazol-5-yl, 2,6-dimethyl-thiazolo [3,2-b] [1,2,4]triazol-5-yl or 5,6-dihydro-4,5-dimethyl-2(H)-3-pyranonyl;
when Q is 2-methyl-phenyl then Het is other than 2-thienyl, 2-benzofuranyl or 3-pyridyl;
when Q is 4-methoxy-phenyl then Het is other than 2-furanyl, 2-pyrazinyl, 3-pyridyl, 4-pyridyl, 1,2-dihydro-6-methyl-2-oxo-3-cyano-5-pyridyl, 1,2-dihydro-6-ethyl-2-oxo-3-cyano-5-pyridyl, 4-(dimethylamino)-1,2-dihydro-6-methyl-2-oxo-3-cyano-5pyridyl, 1,2-dihydro-4-methoxy-6-methyl-2-oxo-3-cyano-5-pyridyl or 3-amino-6-methyl-2(1H)-5-pyridinonyl;
when Q is 2-methoxy-phenyl then Het is other than 2-pyrazinyl, 5-chloro-2-benzimidazolyl, or 3-pyridyl;
when Q is 4-chloro-phenyl then Het is other than 2-furanyl, 2-thienyl, 5-chloro-2-benzimidazolyl, 2-pyrazinyl, 3-pyridyl, 4-pyridyl or 5,6-dihydro4,5-dimethyl-2(H)-3-pyranonyl;
when Q is 3-chloro-phenyl then Het is other than 2-thienyl, 3-pyridyl or 1,2-dihydro-6-methyl-2-oxo-3-cyano-5-pyridyl;
when Q is 2-chloro-phenyl then Het is other than 2-thienyl;
when Q is 3-methyl-phenyl then Het is other than 2-thienyl or 3-pyridyl;
when Q is 2,3-dichloro-phenyl then Het is other than 3-pyridyl;
when Q is 2-ethoxy-phenyl or 3-methoxy-phenyl then Het is other than 2-pyrazinyl;
when Q is 4-bromo-phenyl then Het is other than 2-thienyl, or 5-chloro-2-benzimidazolyl;
when Q is 4-fluoro-phenyl then Het is other than 4-pyridyl;
when Q is 1-naphthyl then Het is other than 2-thienyl, or 3-pyridyl;
when Q is 4-methyl-phenyl then Het is other than 2-furanyl, 2-thienyl, 3-pyridyl, 2-pyrazinyl or 5,6-dihydro-4,5-dimethyl-2(H)-3-pyranonyl;
when Q is 4-ethoxy-phenyl then Het is other than 2-pyrazinyl;
when Q is 2-naphthyl, 2-carboxy-phenyl, 3-carboxy-phenyl, 4-carboxy-phenyl, 4-amino-phenyl or 3-chloro-2,6-dinitro4-trifluoromethyl-phenyl then Het is other than 2-thienyl;
when Q is 4-benzenesulfonamide then Het is other than 2-furanyl, or 1,2,3,4-tetra-hydro-2,4-dioxo-5-pyrimidinyl;
when Q is N-methyl4-benzenesulfonamide then Het is other than 3-thienyl;
when Q is N-butyl4-benzenesulfonamide then Het is other than 2-furanyl;
when Q is 2-pyridyl then Het is other than 2-pyrazinyl;

when Q is 3-pyridyl then Het is other than 2-thienyl, 3-pyridyl, 4-pyridyl or 1,2-dihydro-6-methyl-2-oxo-3-cyano-5-pyridyl;

when Q is 2,4-dichloro-phenyl then Het is other than 2-pyrazinyl, or 4-pyridyl;

when Q is 4-pyridyl then Het is other than 3-quinolinyl or 1,2-dihydro-6-methyl-2-oxo-3-cyano-5-pyridyl;

when Q is 2,4-dimethoxyphenyl, 3,4-dimethoxyphenyl, 4-hydroxyphenyl, 4-methylthiophenyl, or 4-methylsulfinylphenyl then Het is other than 1,2-dihydro-6-methyl-2-oxo-3-cyano-5-pyridyl.

The L or Q radical as described above for the compounds of formula (I) or (I') may be attached to the remainder of the molecule of formula (I) or (I') through any ring carbon or heteroatom as appropriate. For example, when Q is pyridyl, it may be 2-pyridyl, 3-pyridyl or 4-pyridyl.

Lines drawn into ring systems indicate that the bond may be attached to any suitable ring atom. When the ring system is a bicyclic ring system, the bond may be attached to any suitable ring atom of either of the two rings.

As used hereinabove or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{2-6}$alkenyl as a group or part of a group defines straight or branched chain hydrocarbon radicals having from 2 to 6 carbon atoms and having 1 double bond such as ethenyl, propenyl, butenyl, pentenyl, hexenyl, 3-methylbutenyl and the like; $C_{2-6}$alkynyl as a group or part of a group defines straight or branched chain hydrocarbon radicals having from 2 to 6 carbon atoms and having 1 triple bond such as ethynyl, propynyl, butynyl, pentynyl, hexynyl, 3-methylbutynyl and the like; $C_{3-6}$cycloalkyl is generic to cyclopropyl, cyclobutyl, cyclopentyl and cyclohexyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-6}$alkyl, they may be the same or different.

When any variable (e.g. $R^{2a}$) occurs more than one time in any constituent, each definition is independent.

It will be appreciated that some of the compounds of formula (I) or (I') and their N-oxides, addition salts, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of formula (I) or (I') and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) or (I') and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I) or (I') are obviously intended to be embraced within the scope of this invention.

For therapeutic use, salts of the compounds of formula (I) or (I') are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I) or (I') are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) or (I') containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like.

Conversely the salt form can be converted by treatment with acid into the free acid form.

The term addition salt as used hereinabove also comprises the solvates which the compounds of formula (I) or (I') as well as the salts thereof, are able to form. Such solvates are for example hydrates, alcoholates and the like.

The term "quaternary amine" as used hereinbefore defines the quaternary ammonium salts which the compounds of formula (I) or (I') are able to form by reaction between a basic nitrogen of a compound of formula (I) or (I') and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

Some of the compounds of formula (I) or (I') may also exist in their tautomeric form. Such forms although not explicitly indicated in the above formula are intended to be included within the scope of the present invention.

In particular, the radical Het as defined hereinabove may be a radical of formula

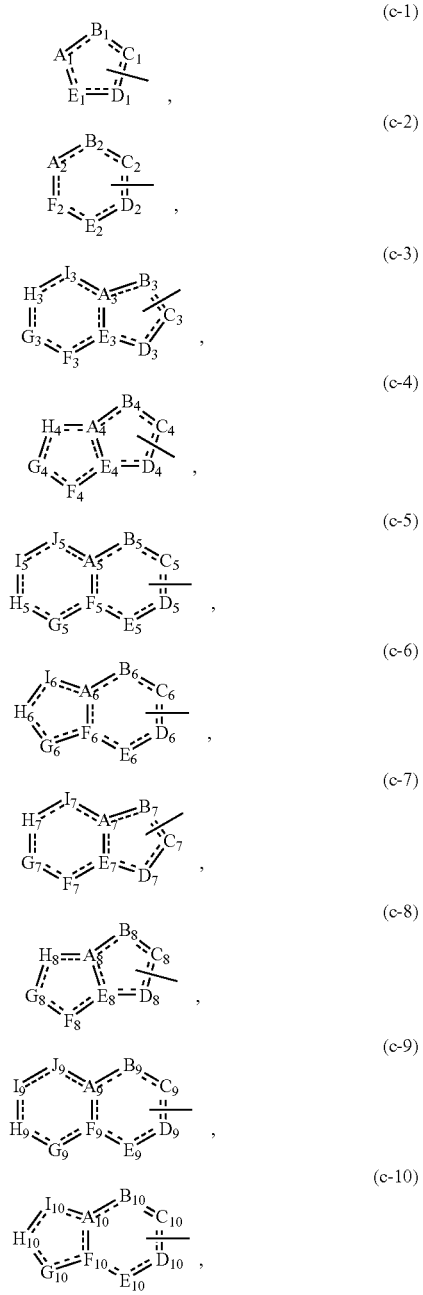

with $A_1$, $B_1$, $C_1$, $D_1$ and $E_1$, each independently being selected where possible from CH, N, NH, O or S, provided that from 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-4}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 4, and wherein each dotted line may represent, where possible, an additional bond, provided that two double bonds are present;

with $A_2$, $B_2$, $C_2$, $D_2$, $E_2$ and $F_2$, each independently being selected where possible from CH, N, O or S, provided that from 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 4, and wherein each dotted line may represent, where possible, an additional bond, provided that at least two double bonds are present;

with $A_3$ and $E_3$, each independently being selected where possible from C, CH or N, and $B_3$, $C_3$ and $D_3$, each independently and where possible being selected from CH, $CH_2$, N, NH, O or S, and $F_3$, $G_3$, $H_3$ and $I_3$, each independently and where possible being selected from $CH_2$ or CH, provided that from 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-4}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the five-membered ring contains two double bonds;

with $A_4$ and $E_4$, each independently being selected where possible from C, CH or N, and $B_4$, $C_4$ and $D_4$, each independently and where possible being selected from CH, $CH_2$, N, NH, O or S, and $F_4$, $G_4$, and $H_4$, each independently and where possible being selected from $CH_2$ or CH, provided that from 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, C! 6alkyloxy, $C_{1-6}$alkyloxycarbonyl, $C_{1-6}$alkylcarbonyloxy, aminocarbonyl, mono- or di($C_{1-4}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the five-membered ring consisting of $A_4$-$B_4$-$C_4$-$D_4$-$E_4$ contains two double bonds;

with $A_5$ and $F_5$, each independently being selected where possible from C, CH or N, and $B_5$, $C_5$, $D_5$ and $E_5$, each independently and where possible being selected from CH, $CH_2$, N, O or S, and $G_5$, $H_5$, $I_5$ and $J_5$, each independently and where possible being selected from $CH_2$ or CH, provided that form 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the six-membered ring consisting of $A_5$-$B_5$-$C_5$-$D_5$-$E_5$-$F_5$ contains at least two double bonds;

with $A_6$ and $F_6$, each independently being selected where possible from C, CH or N, and $B_6$, $C_6$, $D_6$ and $E_6$, each independently and where possible being selected from CH, $CH_2$, N, O or S, and $G_6$, $H_6$ and $I_6$, each independently and where possible being selected from $CH_2$ or CH, provided that from 1 up to 4 heteroatoms are present, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the six-membered ring contains at least two double bonds;

with $A_7$ and $E_7$, each independently being selected where possible from C, CH or N, and $B_7$, $C_7$ and $D_7$, each independently and where possible being selected from CH, $CH_2$, N, NH, O or S, and $F_7$, $G_7$, $H_7$ and $I_7$, each independently and where possible being selected from CH, $CH_2$, N, NH, O or S, provided that the bicyclic ring contains in total from 2 up to 6 heteroatoms with at least one heteroatom in the five-membered ring and at least one heteroatom in the remainder, i.e. $F_7$-$G_7$-$H_7$-$I_7$, of the fused six-membered ring, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_1$alkyloxycarbonyl, $C_1$alkylcarbonyloxy, aminocarbonyl, mono- or di($C_1$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the five-membered ring contains two double bonds;

with $A_8$ and $E_8$, each independently being selected where possible from C, CH or N, and $B_8$, $C_8$, and $D_8$, each independently and where possible being selected from CH, $CH_2$, N, NH, O or S, and $F_8$, $G_8$, and $H_8$, each independently and where possible being selected from CH, $CH_2$, N, NH, O or S, provided that the bicyclic ring contains in total from 2 up to 6 heteroatoms with at least one heteroatom in the five-membered ring consisting of $A_8$-$B_8$-$C_8$-$D_8$-$E_8$ and at least one heteroatom in the remainder, i.e. $F_8$-$G_8$-$H_8$, of the other, fused five-membered ring, and wherein each C or N atom, where possible, may optionally be substituted with halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$ alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$ alkyl)amino-C(=O)—NH—, said substituents being limited to a total of 6, and wherein each dotted line may represent, where possible, an additional bond, provided that the five-membered ring consisting of $A_8$-$B_8$-$C_8$-$D_8$-$E_8$ contains two double bonds;

with $A_9$ and $F_9$, each independently being selected where possible from C, CH or N, and $B_9$, $C_9$, $D_9$ and $E_9$, each independently and where possible being selected from CH, $CH_2$, N, O or S, and $G_9$, $H_9$, $I_9$ and $J_9$, each independently and where possible being selected from CH, $CH_2$, N, NH, O or S, provided that the bicyclic ring contains in total from 2 up to 6 heteroatoms with at least one heteroatom in the six-membered ring consisting of $A_9$-$B_9$-$C_9$-$D_9$-$E_9$-$F_9$ and at least one heteroatom in the remainder, i.e. $G_9$-$H_9$-$I_9$-$J_9$, of the other, fused six-membered ring, and wherein each C or N atom, where possible, may optionally be substituted with halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$ alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the six-membered ring consisting of $A_9$-$B_9$-$C_9$-$D_9$-$E_9$-$F_9$ contains at least two double bonds;

with $A_{10}$ and $F_{10}$, each independently being selected where possible from C, CH or N, and $B_{10}$, $C_{10}$, $D_{10}$ and $E_{10}$, each independently and where possible being selected from CH, $CH_2$, N, O or S, and $G_{10}$, $H_{10}$ and $I_{10}$, each independently and where possible being selected from CH, $CH_2$, N, NH, O or S, provided that the bicyclic ring contains in total from 2 up to 6 heteroatoms with at least one heteroatom in the six-membered ring and at least one heteroatom in the remainder, i.e. $G_{10}$-$H_{10}$-$I_{10}$, of the fused five-membered ring, and wherein each C or N atom, where possible, may optionally be substituted with halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—, said substituents being limited to a total of 6, and wherein each dotted line may represent, where possible, an additional bond, provided that the six-membered ring contains at least two double bonds.

More in particular, the radical Het as defined hereinabove may be a monocyclic heterocycle comprising furanyl, thienyl, pyrrolyl, oxazolyl, thiazolyl, imidazolyl, isoxazolyl, isothiazolyl, pyrazolyl, oxadiazolyl, thiadiazolyl, triazolyl, 1-pyridyl, 2-pyridyl, 3-pyridyl, 4-pyridyl, pyrazinyl, pyridazinyl, pyrimidinyl, pyranyl, triazinyl, tetrazolyl, with each monocyclic heterocycle optionally substituted with, where possible, one, two, three or four substituents selected from halo, hydroxy, amino, cyano, carboxyl, mono- or di($C_{1-4}$alkyl)amino, $C_{1-6}$alkyl, $C_{1-6}$alkyl substituted with $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—; or Het may also represent a bicyclic heterocycle comprising benzofuranyl, benzothienyl, benzthiazolyl, benzoxazinyl, benzoxazinonyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, naphthalenyl, quinolinyl, isoquinolinyl, cinnolinyl, phthalazinyl, quinoxalinyl, quinazolinyl, naphthiridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolo-triazinyl, pyrazolotriazinyl, oxazolotriazinyl, thiazolotriazinyl;, imidazotriazinylf, oxadiazolotriazinyl, thiadiazolotriazinyl, triazolotriazinyl, with each bicyclic heterocycle optionally substituted with, where possible, up to 6 substituents selected from halo, hydroxy, amino, cyano, carboxyl, mono- or di($C_{1-4}$alkyl)amino, $C_{1-6}$alkyl, $C_{1-6}$alkyl substituted with $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—.

In particular, the present invention relates to the use of a compound for the manufacture of a medicament for the prevention or the treatment of diseases mediated through cytokines, wherein the compound is a compound of formula

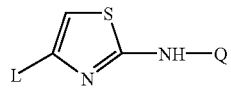

(I')

a N-oxide, a pharmaceutically acceptable addition salt, a quaternary amine and a stereochemically isomeric form thereof, wherein Q is $C_{3-6}$cycloalkyl, phenyl, naphthyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxy; azido; amino; mono- or di($C_{1-6}$alkyl) amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo-$C_{1-6}$alkylcarbonyl; $C_{1-4}$alkyl-S(=O)$_n$— or $R^1HN$—S(=O)$_n$—;

or

Q is a radical of formula

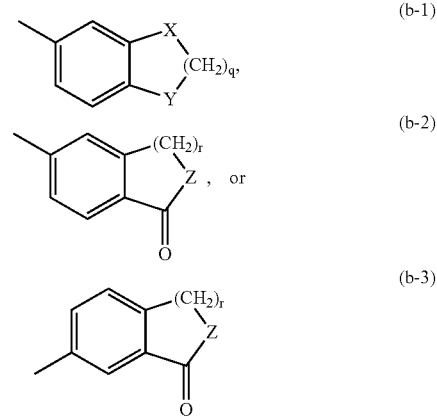

wherein X and Y each independently are O, $NR^3$, $CH_2$ or S, with $R^3$ being hydrogen or $C_{1-4}$alkyl;

q is an integer with value 1 to 4;

Z is O or $NR^4$ with $R^4$ being hydrogen or $C_{1-4}$alkyl;

r is an integer with value 1 to 3;

n is an integer with value 1 or 2;

$R^1$ represents hydrogen, or a radical of formula

(a-1)

with A being O, S or a bivalent radical of formula —$CR^{2a}$=N— with $CR^{2a}$ attached to N of formula (a-1); and $R^{2a}$ being hydrogen, $C_{1-6}$alkyl or $C_{1-6}$alkyloxy;

L is Het;

Het is (i) an optionally substituted five- or six-membered heterocyclic ring containing at least two double bonds and containing 1, 2, 3 or 4 heteroatoms each independently being selected where possible from N, S or O;

(ii) an optionally substituted five- or six-membered heterocyclic ring containing at least two double bonds and containing 1, 2, 3 or 4 heteroatoms each independently being selected where possible from N, S or O and being fused through 2 carbon atoms, 2 nitrogen atoms or 1 carbon and 1 nitrogen atom with another optionally substituted five- or six-membered ring, which contains, apart from the atoms in common with the first ring, only carbon atoms; the latter ring may be unsaturated, partially unsaturated or saturated;

(iii) an optionally substituted five- or six-membered heterocyclic ring containing at least two double bonds and at least one heteroatom and being fused through 2 carbon atoms, 2 nitrogen atoms or 1 carbon and 1 nitrogen atom with another optionally substituted five- or six-membered heterocyclic ring, which contains, apart from the atoms in common with the first ring, at least one heteroatom; the latter ring may be unsaturated, partially unsaturated or saturated; said bicyclic ring system contains in total from 2 up to 6 heteroatoms, each independently being selected where possible from N, S or O;

wherein Het being a monocyclic ring system may optionally be substituted with up to 4 substituents, and wherein Het being a bicyclic ring system may optionally be substituted with up to 6 substituents, said substituents each independently being selected from halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$ alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$ alkyl)amino-C(=O)—NH—;

aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino;

provided that Het is other than optionally substituted isothiazolyl, 2-pyridyl, benzthiazolyl, benzoxazinyl and benzoxazinonyl.

More in particular, the present invention relates to the use of a compound for the manufacture of a medicament for the prevention or the treatment of diseases mediated through cytokines, wherein the compound is a compound of formula

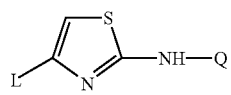

(I')

a N-oxide, a pharmaceutically acceptable addition salt, a quaternary amine and a stereochemically isomeric form thereof, wherein Q is $C_{3-6}$cycloalkyl, phenyl, naphthyl, pyridyl, pyrimidinyl, pyrazinyl, pyridazinyl, benzthiazolyl, benzoxazolyl, benzimidazolyl, indazolyl, or imidazopyridyl, each of said rings optionally being substituted with up to three substituents each independently selected from halo; hydroxy; cyano; carboxy; azido; amino; mono- or di($C_{1-6}$alkyl) amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo-$C_{1-6}$alkylcarbonyl; $C_{1-4}$alkyl-S (=O)$_n$— or $R^1$HN—S(=O)$_n$—;

or

Q is a radical of formula

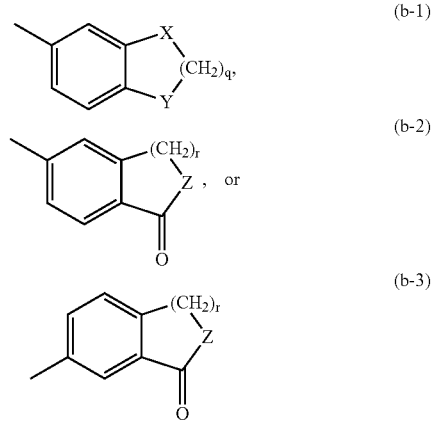

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3;
n is an integer with value 1 or 2;
$R^1$ represents hydrogen, or a radical of formula

with A being O, S or a bivalent radical of formula —$CR^{2a}$=N— with $CR^{2a}$ attached to N of formula (a-1); and
$R^{2a}$ being hydrogen, $C_{1-6}$alkyl or $C_{1-6}$alkyloxy;
L is Het;
Het is (i) an optionally substituted five- or six-membered heterocyclic ring containing at least two double bonds and containing 1, 2, 3 or 4 heteroatoms each independently being selected where possible from N, S or O;
(ii) an optionally substituted five- or six-membered heterocyclic ring containing at least two double bonds and containing 1, 2, 3 or 4 heteroatoms each independently being selected where possible from N, S or O and being fused through 2 carbon atoms, 2 nitrogen atoms or 1 carbon and 1 nitrogen atom with another optionally substituted five- or six-membered ring, which contains, apart from the atoms in common with the first ring, only carbon atoms; the latter ring may be unsaturated, partially unsaturated or saturated;
(iii) an optionally substituted five- or six-membered heterocyclic ring containing at least two double bonds and at least one heteroatom and being fused through 2 carbon atoms, 2 nitrogen atoms or 1 carbon and 1 nitrogen atom with another optionally substituted five- or six-membered heterocyclic ring, which contains, apart from the atoms in common with the first ring, at least one heteroatom; the latter ring may be unsaturated, partially unsaturated or saturated; said bicyclic ring system contains in total from 2 up to 6 heteroatoms, each independently being selected where possible from N, S or O;

wherein Het being a monocyclic ring system may optionally be substituted with up to 4 substituents, and wherein Het being a bicyclic ring system may optionally be substituted with up to 6 substituents, said substituents each independently being selected from halo, hydroxy, amino, cyano, carboxyl, mono- or di($C_{1-4}$ alkyl)amino, $C_{1-6}$alkyl, $C_{1-6}$alkyl substituted with hydroxy or $C_{1-4}$alkyloxy or amino or mono- or di($C_{1-4}$ alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$ alkyl)amino-C(=O)—NH—;

aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, mono- or di($C_{1-6}$alkyl)amino;

provided that

Het is other than optionally substituted isothiazolyl, 2-pyridyl, benzthiazolyl, benzoxazinyl and benzoxazinonyl.

when Q is phenyl substituted with hydroxy or $C_{1-6}$alkyloxy and carboxy or $C_{1-6}$alkyloxycarbonyl then Het is other than 3-pyridyl or 4-pyridyl;

when Q is phenyl then Het is other than 2-thienyl, 2-furanyl, 5-bromo-2-benzofuranyl, 1,2-dihydro-6-methyl-2-oxo-3-cyano-5-pyridyl, 2-benzofuranyl, 5-chloro-2-benzimidazolyl, 2-benzimidazolyl, 3-pyridyl, 4-pyridyl, 6-methyl-thiazolo [3,2-b] [1,2,4]triazol-5-yl, 2,6-dimethyl-thiazolo [3,2-b] [1,2,4]triazol-5-yl or 5,6-dihydro-4,5-dimethyl-2(H)-3-pyranonyl;

when Q is 2-methyl-phenyl then Het is other than 2-thienyl, 2-benzofuranyl or 3-pyridyl;

when Q is 4-methoxy-phenyl then Het is other than 2-furanyl, 2-pyrazinyl, 3-pyridyl, 4-pyridyl, 1,2-dihydro-6-methyl-2-oxo-3-cyano-5-pyridyl, 1,2-dihydro-6-ethyl-2-oxo-3-cyano-5-pyridyl, 4-(dimethylamino)-1,2-dihydro-6-methyl-2-oxo-3-cyano-5-pyridyl, 1,2-dihydro-4-methoxy-6-methyl-2-oxo-3-cyano-5-pyridyl or 3-amino-6-methyl-2(1H)-5-pyridinonyl;

when Q is 2-methoxy-phenyl then Het is other than 2-pyrazinyl, 5-chloro-2-benzimidazolyl, or 3-pyridyl;

when Q is 4-chloro-phenyl then Het is other than 2-furanyl, 2-thienyl, 5-chloro-2-benzimidazolyl, 2-pyrazinyl, 3-pyridyl, 4-pyridyl or 5,6-dihydro4,5-dimethyl-2(H)-3-pyranonyl;

when Q is 3-chloro-phenyl then Het is other than 2-thienyl, 3-pyridyl or 1,2-dihydro-6-methyl-2-oxo-3-cyano-5-pyridyl;

when Q is 2-chloro-phenyl then Het is other than 2-thienyl;

when Q is 3-methyl-phenyl then Het is other than 2-thienyl or 3-pyridyl;

when Q is 2,3-dichloro-phenyl then Het is other than 3-pyridyl;

when Q is 2-ethoxy-phenyl or 3-methoxy-phenyl then Het is other than 2-pyrazinyl;

when Q is 4-bromo-phenyl then Het is other than 2-thienyl, or 5-chloro-2-benzimidazolyl;

when Q is 4-fluoro-phenyl then Het is other than 4-pyridyl;

when Q is 1-naphthyl then Het is other than 2-thienyl, or 3-pyridyl;

when Q is 4-methyl-phenyl then Het is other than 2-furanyl, 2-thienyl, 3-pyridyl, 2-pyrazinyl or 5,6-dihydro-4,5-dimethyl-2(H)-3-pyranonyl;

when Q is 4-ethoxy-phenyl then Het is other than 2-pyrazinyl;

when Q is 2-naphthyl, 2-carboxy-phenyl, 3-carboxy-phenyl, 4-carboxy-phenyl, 4-amino-phenyl or 3-chloro-2,6-dinitro-4-trifluoromethyl-phenyl then Het is other than 2-thienyl;

when Q is 4-benzenesulfonamide then Het is other than 2-furanyl, or 1,2,3,4-tetra-hydro-2,4-dioxo-5-pyrimidinyl;

when Q is N-methyl-4-benzenesulfonamide then Het is other than 3-thienyl;

when Q is N-butyl-4-benzenesulfonamide then Het is other than 2-furanyl;

when Q is 2-pyridyl then Het is other than 2-pyrazinyl;

when Q is 3-pyridyl then Het is other than 2-thienyl, 3-pyridyl, 4-pyridyl or 1,2-dihydro-6-methyl-2-oxo-3-cyano-5-pyridyl;

when Q is 2,4-dichloro-phenyl then Het is other than 2-pyrazinyl, or 4-pyridyl;

when Q is 4-pyridyl then Het is other than 3quinolinyl or 1,2-dihydro-6-methyl-2-oxo-3-cyano-5-pyridyl;

when Q is 2,4-dimethoxyphenyl, 3,4-dimethoxyphenyl, 4-hydroxyphenyl, 4-methylthiophenyl, or 4-methylsulfinylphenyl then Het is other than 1,2-dihydro-6-methyl-2-oxo-3-cyano-5-pyridyl.

The present invention also relates to the use of a compound for the manufacture of a medicament for the prevention or the treatment of diseases mediated through cytokines, wherein the compound is a compound of formula

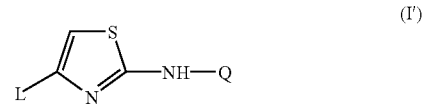

(I')

a N-oxide, a pharmaceutically acceptable addition salt, a quaternary amine and a stereochemically isomeric form thereof, wherein Q is phenyl, naphthyl, pyridyl, pyrimidinyl, pyrazinyl or pyridazinyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$ alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo-$C_{1-6}$alkylcarbonyl; $C_{1-4}$alkyl-S(=O)$_n$— or $R^1HN$—S(=O)$_n$—;

or

Q is a radical of formula

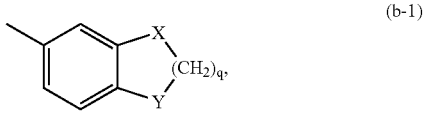

(b-1)

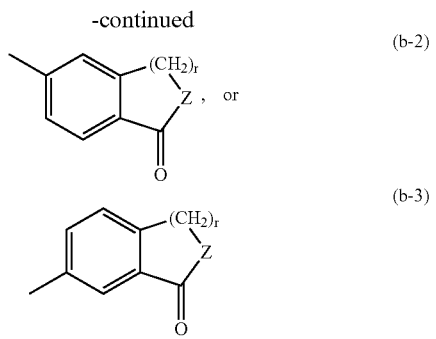

wherein X and Y each independently are O, NR$^3$, CH$_2$ or S, with R$^3$ being hydrogen or C$_{1-4}$alkyl;
q is an integer with value 1 to 4;
Z is O or NR$^4$ with R$^4$ being hydrogen or C$_{1-4}$alkyl;
r is an integer with value 1 to 3;
n is an integer with value 1 or 2;
R$^1$ represents hydrogen, or a radical of formula

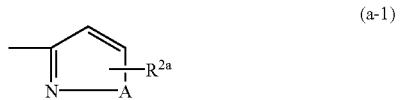

with A being O, S or a bivalent radical of formula —CR$^{2a}$=N— with CR$^{2a}$ attached to N of formula (a-1); and
R$^{2a}$ being hydrogen, C$_{1-6}$alkyl or C$_{1-6}$alkyloxy;
L is phenyl, optionally substituted with up to 4 substituents each independently being selected from halo, hydroxy, amino, mono or di(C$_{1-4}$alkyl)amino, C$_{1-6}$alkyl, polyhaloC$_{1-6}$alkyl or C$_{1-6}$alkyloxy; or
L is Het;
Het is (i) an optionally substituted five- or six-membered heterocyclic ring containing at least two double bonds and containing 1, 2, 3 or 4 heteroatoms each independently being selected where possible from N, S or O;
(ii) an optionally substituted five- or six-membered heterocyclic ring containing at least two double bonds and containing 1, 2, 3 or 4 heteroatoms each independently being selected where possible from N, S or O and being fused through 2 carbon atoms, 2 nitrogen atoms or 1 carbon and 1 nitrogen atom with another optionally substituted five- or six-membered ring, which contains, apart from the atoms in common with the first ring, only carbon atoms; the latter ring may be unsaturated, partially unsaturated or saturated;
(iii) an optionally substituted five- or six-membered heterocyclic ring containing at least two double bonds and at least one heteroatom and being fused through 2 carbon atoms, 2 nitrogen atoms or 1 carbon and 1 nitrogen atom with another optionally substituted five- or six-membered heterocyclic ring, which contains, apart from the atoms in common with the first ring, at least one heteroatom; the latter ring may be unsaturated, partially unsaturated or saturated; said bicyclic ring system contains in total from 2 up to 6 heteroatoms, each independently being selected where possible from N, S or O;
wherein Het being a monocyclic ring system may optionally be substituted with up to 4 substituents, and wherein Het being a bicyclic ring system may optionally be substituted with up to 6 substituents, said substituents each independently being selected from halo, hydroxy, amino, mono or di(C$_{1-4}$alkyl)armino, C$_{1-6}$alkyl, polyhaloC, alkyl or C$_{1-6}$alkyloxy;
aryl is phenyl, optionally substituted with up to five substituents each independently selected from halo, hydroxy, C$_{1-6}$alkyl, C$_{1-6}$alkyloxy, C$_{1-6}$alkylthio, cyano, nitro, amino, mono- or di(C$_{1-6}$alkyl)amino.

An interesting group comprises those compounds of formula (I) or (I') wherein L is Het and Het is defined as hereinabove provided that Het is other than benzimidazolyl; benzofuranyl; thiazolotriazolyl; quinolinyl; pyrazinyl; dioxopyrimidinyl; pyrimidinyl; pyridazinyl; pyranonyl; thienyl; furanyl; a 5 or 6-membered heterocyclic group containing one nitrogen atom such as for example pyridyl.

Also an interesting group comprises those compounds of formula (I) or (I') wherein L is Het and Het being a monocyclic ring system may optionally be substituted with up to 4 substituents, or Het being a bicyclic ring system may optionally be substituted with up to 6 substituents, said substituents each independently being selected from halo, hydroxy, amino, mono or di(C$_{1-4}$alkyl)amino, C$_{1-6}$alkyl, polyhaloC$_{1-6}$alkyl or C$_{1-6}$alkyloxy.

A further interesting group comprises those compounds of formula (I) or (I') wherein L is imidazolyl, imidazothiazolyl, pyrimidinyl, thienyl, thiazolyl, furanyl, 3-pyridyl, 4-pyridyl, pyrazolyl, indolyl, indazolyl, quinolinyl, benzofuranyl, pyrrolopyridyl, imidazopyridyl, imidazopyrazinyl, imidazopyrimidinyl, imidazopyridazinyl, pyrazolopyridyl, with each heterocycle optionally substituted with one, two, three or four substituents selected from halo, amino, C$_{1-6}$alkyl, polyhaloC$_{1-6}$alkyl, aminocarbonyl or C$_{1-6}$alkyl-C(=O)—NH—.

Still another interesting group includes those compounds of formula (I) or (I') wherein L is 3-pyridyl, 4-pyridyl, thiazolyl, pyrazolyl, indolyl, indazolyl, quinolinyl, benzofuranyl, pyrrolopyridyl, imidazopyridyl, iridazopyrazinyl, imidazopyrimidinyl, imidazopyridazinyl, pyrazolopyridyl, with each heterocycle optionally substituted with one, two, three or four substituents selected from halo, amino, or C$_{1-6}$alkyl.

Yet a further interesting group comprises those compounds of formula (I) or (I') wherein L is imidazolyl, imidazothiazolyl, pyrimidinyl, pyrazolyl, indolyl, indazolyl, pyrrolopyridyl, imidazopyridyl, imidazopyrazinyl, imidazopyrimidinyl, imidazopyridazinyl, pyrazolopyridyl, with each heterocycle optionally substituted with one, two, three or four substituents selected from halo, amino, C$_{1-6}$alkyl, polyhaloC$_{1-6}$alkyl, aminocarbonyl or C$_{1-6}$alkyl-C(=O)—NH—.

Again an interesting group comprises those compounds of formula (I) or (I') wherein L is Het and Het is as defined hereinabove provided that Het is other than pyrazolyl, benzofuranyl, 2-imidazo[1,2-a]pyridyl, imidazopyridazinyl, indazolyl, pyrazinyl, 4-pyrimidinyl, thiazolyl, imidazolyl.

Also an interesting group comprises those compounds of formula (I) or (I') wherein L is Het and Het is as defined hereinabove provided that Het is other than pyrazolyl, benzofuranyl, 2-imidazo[1,2-a]pyridyl, imidazopyridazinyl, indazolyl, pyrazinyl, pyrimidinyl, pyridazinyl, thiazolyl, imidazolyl, benzimidazolyl, thiazolotriazolyl, quinolinyl, dioxopyrimidinyl, pyranonyl, a 5 or 6-membered heterocyclic group containing one nitrogen atom, thienyl, furanyl.

Again an interesting group comprises those compounds of formula (I) or (I') wherein L is Het and Het is indolyl, 3-imidazo[1,2-a]pyridyl, 3-imidazo[1,5-a]pyridyl, 3-pyridyl, quinolinyl, imidazopyrimidinyl, imidazopyrazinyl, imidazothiazolyl, 5-pyrimidinyl, furanyl, thiazolyl, imidazolyl, pyrrolopyridyl, pyrazolopyridyl.

A further interesting group comprises those compounds of formula (I) or (I') wherein L is Het and Het is indolyl, 3-imidazo[1,2-a]pyridyl, 3-imidazo[1,5-a]pyridyl, imidazopyrimidinyl, imidazopyrazinyl, imidazothiazolyl, pyrrolopyridyl, pyrazolopyridyl.

Further preferred compounds are those compounds of formula (I) or (I') wherein L is Het and Het is 3-imidazo[1,2-a]pyridyl, 3-imidazo[1,5-a]pyridyl, imidazothiazolyl, 5-pyrimidinyl, substituted 3- or 4-pyridyl.

Yet further preferred compounds are those compounds of formula (I) or (I') wherein L is 3-imidazo[1,2-a]pyridyl, 3-imidazo[1,5-a]pyridyl, imidazothiazolyl, 3-pyridyl or pyrrolopyridyl.

Also preferred compounds are those compounds of formula (I) or (I') wherein L is 3-fluorophenyl or 3,5-difluorophenyl.

Also preferred are those compounds of formula (I) or (I') wherein L is Het and Het is as described hereinabove provided that the atom(s) adjacent to the atom with which Het is linked to the remainder of the molecule of formula (I) and which does (do) not form part of both rings in case of a bicyclic heterocycle, is (are) other than nitrogen.

Again preferred compounds are those compounds of formula (I) or (I') wherein L is 3-halophenyl.

Also an interesting group comprises those compounds of formula (I) or (I') wherein Q is phenyl, naphthyl, pyridyl, pyrimidinyl, pyrazinyl, pyridazinyl, benzthiazolyl, benzoxazolyl, benzimidazolyl, indazolyl or imidazopyridyl, each of said rings optionally being substituted with up to three substituents each independently selected from halo; hydroxy; cyano; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo$C_{1-6}$alkyloxy; polyhalo$C_{1-6}$alkylcarbonyl or $C_{1-4}$alkyl-$S(=O)_n$—; or Q is a radical of formula

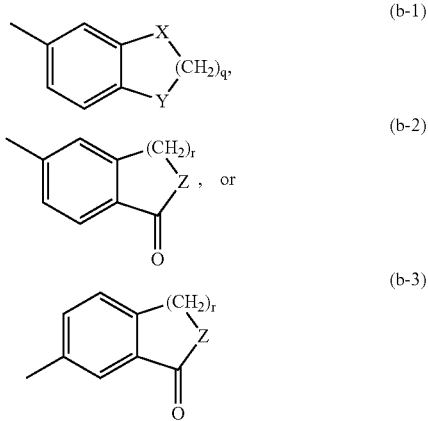

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3.

A further interesting group comprises those compounds of formula (I) or (I') wherein Q is phenyl, naphthyl, pyridyl, pyrimidinyl, pyrazinyl or pyridazinyl, each of said rings optionally being substituted with up to three substituents each independently selected from halo; hydroxy; cyano; carboxy; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino, $C_{1-6}$alkyloxy; $C_{1-6}$alkylthio; $C_{1-6}$alkylcarbonyl; $C_{1-6}$alkyloxycarbonyl; $C_{1-6}$alkylcarbonylamino; aryl$C_{1-6}$ alkyloxy; aryloxy; polyhalo$C_{1-6}$alkyl; polyhalo$C_{1-6}$alkyloxy; polyhalo$C_{1-6}$alkylcarbonyl; $C_{1-4}$alkyl-$S(=O)_n$— or $R^1HN-S(=O)_n$—; or Q is a radical of formula

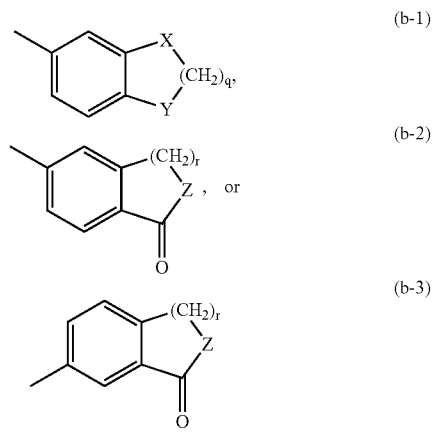

wherein X and Y each independently are O, $NR^3$, $CH_2$ or S, with $R^3$ being hydrogen or $C_{1-4}$alkyl;
q is an integer with value 1 to 4;
Z is O or $NR^4$ with $R^4$ being hydrogen or $C_{1-4}$alkyl;
r is an integer with value 1 to 3.

Another interesting group comprises those compounds of formula (I) or (I') wherein Q is 3-pyridyl, 4-pyridyl, naphthalenyl, $C_{3-6}$cycloalkyl, phenyl, 1,3-benzodioxolyl, 2,3-dihydro-benzofuranyl, 2,3-dihydro-1,4-benzodioxinyl, benzthiazolyl, indazolyl, benzimidazolyl or imidazopyridyl.

Also particular compounds are those compounds of formula (I) or (I') wherein Q is phenyl, 3-pyridyl, 4-pyridyl, benzthiazolyl or imidazopyridyl, in particular phenyl, each of said rings being optionally substituted with up to three substituents selected from halo, cyano, $C_{1-6}$alkyl, $C_{1-6}$alkyloxy or polyhalo$C_{1-6}$alkyl.

Each of the above-mentioned interesting groups of compounds of formula (I) or (I') describing a particular definition of L may be combined with each of the above-mentioned interesting groups of compounds of formula (I) or (I') describing a particular definition of Q.

Preferred compounds are selected from the group consisting of 2-thiazolamine, 4-imidazo[1,2-a]pyridin-3-yl-N-[3-(trifluoromethyl)phenyl];

2-thiazolamine, 4-imidazo[1,2-a]pyridin-3-yl-N-[4-(trifluoromethyl)phenyl];

2-thiazolamine, 4-(3-pyridinyl)-N-[3-(trifluoromethyl)phenyl];

2-thiazolamine, N-(3-chlorophenyl)-4-imidazo[1,2-a]pyridin-3-yl;

2-thiazolaamine, 4-imidazo[1,2-a]pyridin-3-yl-N-(3-methylphenyl);

2-thiazolamine, 4-imidazo[1,2-a]pyridin-3-yl-N-[3-(methylthio)phenyl];

2-thiazolaamine, N-(4-chlorophenyl)₄-imidazo[1,2-a]pyridin-3-yl;
2-thiazolamine, N-(3-bromophenyl)-4-imidazo[1,2-a]pyridin-3-yl;
2-thiazolamine, N-(2,3-dichlorophenyl)-4-imidazo[1,2-a]pyridin-3-yl;
2-thiazolamine, N-(2,3-dichlorophenyl)₄-(1H-pyrrolo[2,3-b]pyridin-3-yl);
2-thiazolamine, N-(4-bromophenyl)₄-imidazo[1,2-a]pyridin-3-yl;
2-thiazolamine, N-(2,3-dichlorophenyl)₄-imidazo[1,5-a]pyridin-3-yl;
2-thiazolaamine, 4-imidazo[2,1-b]thiazol-5-yl-N-[3-(trifluoromethyl)phenyl];
2-thiazolamine, N-(2,3-dichlorophenyl)₄-imidazo[2,1-b]thiazol-5-yl;
2-thiazolamine, 4-(3-pyridinyl)-N-(3-methyl4-fluorophenyl);
2-thiazolamine, 4-imidazo[1,2-a]pyridin-3-yl-N-(3-methyl4-fluorophenyl);

the N-oxides, pharmaceutically acceptable addition salts, quaternary amines and stereochemically isomeric forms thereof.

Also preferred compounds are selected from the group consisting of
2-thiazolamine, 4-(3-fluorophenyl)-N-phenyl;
2-thiazolamine, 4-(3-fluorophenyl)-N-[4-methoxyphenyl];
2-thiazolamine, 4-(3-fluorophenyl)-N-[4-(trifluoromethyl)phenyl]; and
2-thiazolamine, 4-(3-fluorophenyl)-N-[3-pyridyl];

the N-oxides, pharmaceutically acceptable addition salts, quaternary amines and stereochemically isomeric forms thereof.

In general, the compounds of formula (I) may be prepared by reacting an intermediate of formula (II) or formula (III) or by reacting an intermediate of formula (II) and (III), wherein $W_1$ represents a suitable leaving group, such as a halo atom, e.g. chloro or bromo, with an intermediate of formula (IV) in a suitable reaction-inert solvent, such as an alcohol, e.g. ethanol, or N,N-dimethylformamide.

Compounds of formula (I), wherein L is substituted with amino, said L being represented by $NH_2$-$L_1$, and said compounds by formula (I-a), may be prepared by reacting an intermediate of formula (II), wherein Het is substituted with $C_{1-6}$alkyl-C(=O)—NH—, said Het being represented by $C_{1-6}$alkyl-C(=O)—NH-Het$_1$, and said intermediate being represented by formula (II-a), with an intermediate of formula (IV) in the presence of a suitable acid, such as for example hydrobromic acid and the like, in the presence of a suitable solvent, such as an alcohol, e.g. ethanol and the like, and water.

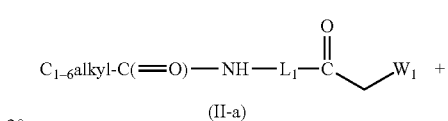

Compounds of formula (I), wherein Q is substituted with amino, said Q being represented by $Q_1$-$NH_2$, and said compounds by formula (I-b), may be prepared by reducing an intermediate of formula (I-b-interm.), wherein Q is substituted with nitro, said Q being represented by $Q_1$-$NO_2$, in the presence of a suitable reducing agent, e.g. hydrogen, optionally in the presence of a suitable catalyst, e.g. palladium-on-charcoal, and a suitable catalyst poison, e.g. a thiophene solution. A suitable solvent for the above reaction is a reaction-inert solvent, for example, an alcohol, e.g. methanol.

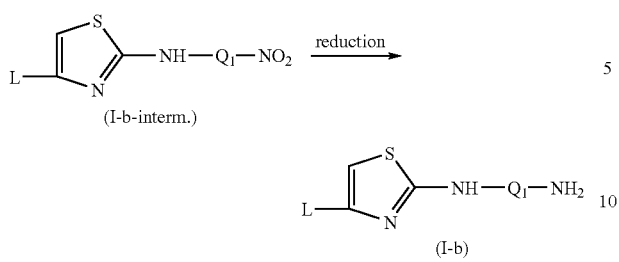

(I-b-interm.) → (I-b)

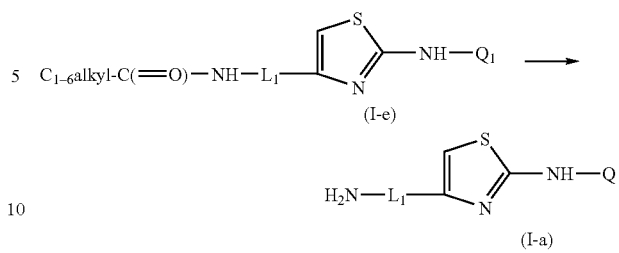

(I-e) → (I-a)

Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I), wherein Q is substituted with cyano, said Q being represented by $Q_1$-CN, and said compounds by formula (I-c), may be converted into a compound of formula (I), wherein Q is substituted with carboxy, said Q being represented by $Q_1$-COOH, and said compound by formula (I-d), by reaction with a suitable acid, such as concentrated hydrochloric acid, in the presence of a suitable reaction-inert solvent, e.g. water.

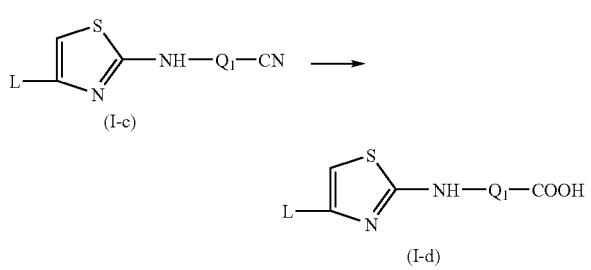

(I-c) → (I-d)

Compounds of formula (I), wherein L is substituted with $C_{1-6}$alkyl-C(=O)—NH—, said Het being represented by $C_{1-6}$alkyl-C(=O)—NH-$Het_1$, and said compounds being represented by formula (I-e), may be converted into a compound of formula (I-a), by reaction with a suitable acid, such as for example hydrobromic acid and the like, in the presence of a suitable solvent, such as water.

In the following paragraphs, there are described several methods of preparing the intermediates in the foregoing preparations. A number of intermediates and starting materials are commercially available or are known compounds which may be prepared according to conventional reaction procedures generally known in the art.

Intermediates of formula (II) can be prepared by reacting an intermediate of formula (V) with a suitable leaving group introducing agent of formula (VI), wherein $W_1$ represents the leaving group and R represents the remaining of the agent, such as for example $W_1$-R representing $Br_2$, in the presence of a suitable solvent, such as a HBr solution, dioxane, acetic acid and the like.

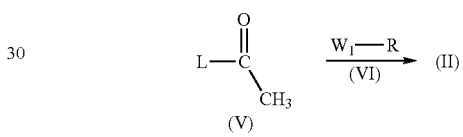

(V) + (VI) → (II)

Alternatively, intermediates of formula (II) may also be prepared by Friedel-Crafts acylation in the presence of a suitable Lewis acid, for example by reacting an intermediate of formula (VII) with an intermediate of formula (VIII), wherein $W_1$ and $W_2$ represent a suitable leaving group, such as a halo atom, e.g. chloro, in the presence of $AlCl_3$ and in the presence of a suitable solvent, e.g. carbon disulfide.

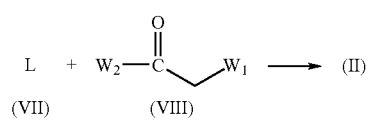

(VII) + (VIII) → (II)

Intermediates of formula (II) may also be prepared by acylating an intermediate of formula (VII-a), i.e. L having an acidic hydrogen atom, with an intermediate of formula (IX), with $W_1$ as defined hereinabove, in the presence of a suitable base, e.g. lithium diisopropylamide, and a suitable reaction-inert solvent, e.g. tetrahydrofuran.

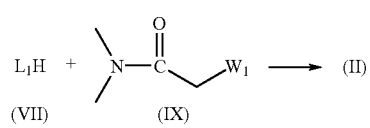

(VII) + (IX) → (II)

Intermediates of formula (II) may also be prepared by reacting an intermediate of formula (XI), with $W_1$ as defined hereinabove, with a suitable acid, such as a HBr solution, in the presence of a suitable solvent, e.g. water.

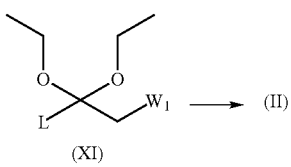

Intermediates of formula (III) may be prepared according to the first reaction procedure described above to prepare an intermediate of formula (II), thus by reacting an intermediate of formula (V) with an intermediate of formula (VI) in the presence of a suitable solvent, e.g. acetic acid, hydrobromic acid or the like.

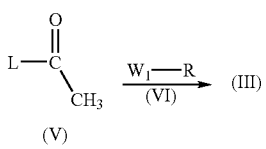

Intermediates of formula (V) may be prepared by reacting an intermediate of formula (XII), wherein $W_3$ is a suitable leaving group, such as a halo atom, e.g. chloro, with an intermediate of formula (XIII) in the presence of N,N-dimethyl-4-pyridinamine and a suitable solvent, such as dichloromethane.

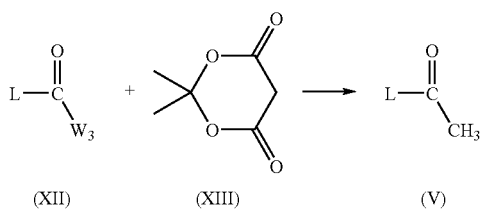

Intermediates of formula (XII), wherein $W_3$ represents chloro, said intermediates being represented by formula (XII-a), can be prepared by reacting an intermediate of formula (XIV) with $SOCl_2$.

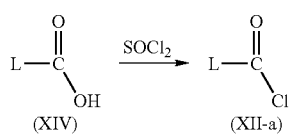

Intermediates of formula (V), wherein L is Het and Het is an imidazo[1,2-a]pyrazinyl moiety as represented by formula (V-a), can be prepared by reacting an intermediate of formula (XV) with an intermediate of formula (XVI), wherein $W_4$ is a suitable leaving group, such as a halo atom, e.g. bromo, in the presence of a suitable reaction-inert solvent, such as an alcohol, e.g. ethanol.

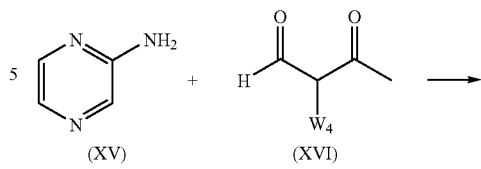

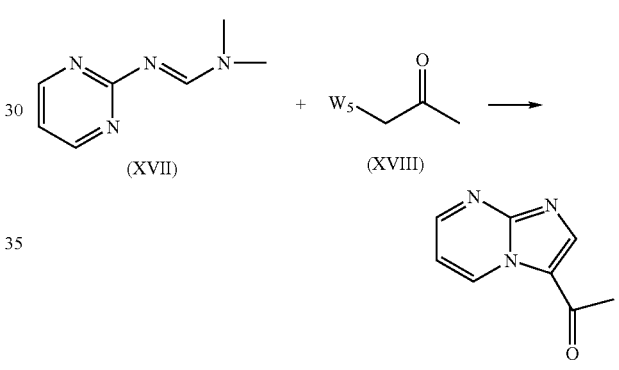

Intermediates of formula (V), wherein L is Het and Het is an imidazo[1,2-a]pyrirnidinyl moiety as represented by formula (V-b), can be prepared by reacting an intermediate of formula (XVII) with an intermediate of formula (XVIII), wherein $W_5$ represents a suitable leaving group, such as a halo atom, e.g. chloro, in the presence of a suitable reaction-inert solvent, such as methylene chloride.

Intermediates of formula (XVII) may be prepared by reacting an intermediate of formula (XIX) with an intermediate of formula (XX) in a reaction-inert solvent, such as toluene.

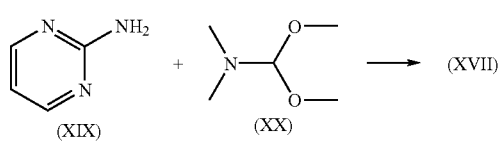

Intermediates of formula (IV) may be prepared by hydrolizing an intermediate of formula (XXI) in the presence of a suitable base, such as for example sodium hydroxide, and in the presence of a suitable solvent, such as an alcohol, e.g. ethanol and the like.

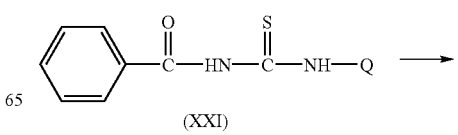

-continued

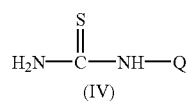

Intermediates of formula (XXI) may be prepared by reacting an intermediate of formula (XXII) with an intermediate of formula (XXI) in the presence of a suitable solvent, such as tetrahydrofuran.

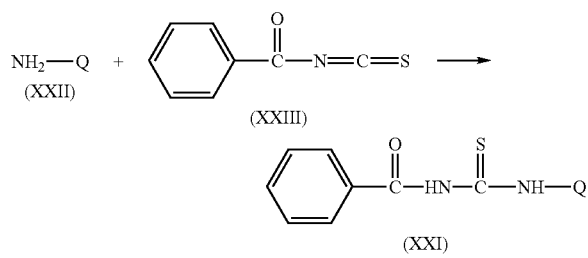

Intermediates of formula (XXII) may be prepared by hydrolyzing an intermediate of formula (XXIV) in the presence of a suitable acid, such as hydrobromic acid, hydrochloric acid, acetic acid and the like, or mixtures thereof, and in the presence of a suitable solvent, such as for example ethyl acetate.

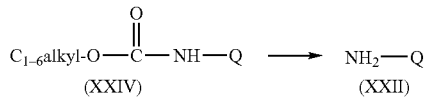

Intermediates of formula (XXIV) may be prepared by reacting an intermediate of formula (XXV) with phosphorazidic acid diphenyl ester in the presence of a suitable base, such as N,N-diethyl-ethanamine, and in the presence of a suitable alcohol such as $C_{1-6}$alkylOH, e.g. ethanol, t-butanol and the like.

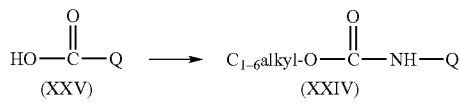

The compounds of the present invention show cytokine production modulating activity, in particular cytokine production inhibitory activity, more in particular proinflammatory cytokine production inhibitory activity. A cytokine is any secreted polypeptide that affects the function of other cells by modulating interactions between cells in the immune or inflammatory response. Examples of cytokines include Interleukin-1 (IL-1) up to Interleukin-18 (IL-18), Tumor Necrosis Factor-alpha (TNFα), Tumor Necrosis Factor-beta (TNF-β). The present compounds also show inhibitory activity on the production of chemotactic cytokines or chemokines responsible for trafficking and activation of leucocytes. A chemokine production inhibited by the compounds of formula (I) or (I') is MCP-1 production (Monocyte Chemotactic Protein 1).

The cytokine production specifically inhibited by the compounds of formula (I) or (I') is TNF-α and/or Interleukin-12 (IL-12) production.

TNF-α is primarily produced by monocytes, macrophages, T and B lymphocytes, neutrophils, mast cells, tumour cells, fibroblasts, keratinocytes, astrocytes, microglial cells, smooth muscle cells and others. This proinflammatory cytokine is established at the pinnacle of proinflammatory cascades; it exerts a key role in the cytokine network with regard to the pathogenesis of many infectious, inflammatory and autoimmune diseases. Excessive or unregulated TNF-α production is implicated in mediating or exacerbating a number of diseases including rheumatoid arthritis, rheumatoid spondylitis, spondyloarthropathies, systemic lupus erythematosus, osteoarthritis, gouty arthritis, juvenile arthritis and other arthritic conditions, polychondritis, sclerodoma, Wegener granulamatosis, dermatomyositis, Steven-Johnson syndrome, idiopatic sprue, endocrine opthalmopathy, Grave's disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupus, phthinoid bronchitis), chronic obstructive airway or pulmonary disease, pulmonary fibrosis, pneumoconiosis (aluminosis,anthracosis, asbestosis, chalicocis, ptilosis, siderosis, silicosis, tobaccosis, byssionosis), tuberculosis, silicosis, exacerbation of airways hyperreactivity to other drug therapy (e.g. aspirin or β-agonist therapy), pulmonary sarcoidosis, bone resorption diseases, meningitis, reperfusion injury, graft versus host reaction, allograft rejections, transplant rejections, fever and myalgias due to infection, such as influenza, cachexia (consequential to, e.g. bacterial, viral or parasitic, infection. or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behqet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL-2 infusion, anti-CD3 antibody infusion, hemodialysis, yellow fever vaccination. TNF-α has also been shown to activate HIV (Human Immune deficiency Virus) replication in monocytes and/or macrophages. Therefore, inhibition of TNF-α production or activity aids in limiting HIV progression. TNF-α also plays a role in other viral infections, such as Hepatitis C, CMV (cytomegalovirus), influenza and herpes virus infections, including herpes simplex virus type-1, herpes simplex virus type-2, varicella-zoster virus, Epstein-Barr virus, human herpes virus-6, -7 and -8, pseudorabies and rhinotracheitis.

IL-12 is produced primarily by monocytes, macrophages and dendritic cells in response to bacteria, bacterial products (lipopolysaccharide) and immune signals. The production of IL-12 is regulated by other cytokines and endogenous mediators produced during inflammatory and immunological responses. IL-12 plays a central role in the immune system. Evidence obtained from animal models and human diseases suggests that inappropriate and protracted production of IL-12 and the ability of IL-12 to induce the generation of T helper 1 cell type responses may be instrumental in the development and maintenance of chronic inflammatory diseases, such as rheumatoid arthritis, collagen induced arthritis, allergic encephalitis, colitis, inflammatory bowel disease, Crohn's disease and multiple sclerosis, and in the triggering of autoimmune disorders, such as diabetes, or graft versus host diseases or shock. The adverse effects also include anemia (haemolytic, aplastic, pure red cell, idiopathic thrombocytopenia), neutropenia, lymphopenia, hepatosplenomegaly with mononuclear cell infiltration and pulmonary edema with interstitial cell infiltrates. Excessive IL-12 production may accelerate the inflammatory progress of a disease, or the onset of the disease, such as rheumatoid arthritis, or it may also augment the disease severity.

Inhibition of TNF-α and/or IL-12 production by the compounds of formula (I) or (I') might offer an interesting, potentially less toxic alternative to non-specific immunosuppression (e.g. corticosteroids) in the treatment of chronic inflammatory and autoimmune diseases. The combined modulation of TNF-α and IL-12 production may ameliorate the treated disease to a greater extent than mono-therapy. The therapeutic effect of combining the suppression of both the immune and the inflammatory arm of a disease may provide additional clinical benefits. The present compounds are also indicated for use as co-therapeutic agents for use in conjunction with immunosuppressive and/or anti-inflammatory drugs, e.g. as potentiators of the therapeutic activity of said drugs, to reduce required dosaging or thus also potential side effects of said drugs. Immunosuppressive and/or anti-inflammatory drugs include for example cyclopeptide, cyclopeptolide or macrolide immunosuppressive or anti-inflammatory drugs, such as drugs belonging to the cyclosporin class, e.g. cyclosporine A or G, tacrolimus substances, ascomycin, rapamycin, glucocorticosteroid drugs, e.g. budesonide, beclamethasone, fluticasone, mometasone.

The compounds of formula (I) or (I') are useful in preventing or treating cytokine mediated diseases, and as such, inhibit, suppress or antagonize the production or activity of proinflammatory cytokines, such as TNF-α and/or IL-12.

Disorders mediated through TNF-α and/or IL-12 refers to any and all disorders and disease states in which TNF-α and/or IL-12 play a role, either by the cytokine itself, or by the cytokine causing another cytokine, such as for example IL-1 or IL-6, or a certain mediator to be released.

Due to their cytokine production inhibitory activity, in particular their proinflammatory cytokine production inhibitory activity, more in particular their TNF-α and/or IL-12 inhibitory activity, the compounds of formula (I) or (I'), their N-oxides, pharmaceutically acceptable addition salts, quaternary amines and stereochemically isomeric forms are useful in the treatment or prevention of diseases or conditions mediated through cytokines, in particular diseases or conditions related to excessive or unregulated production of proinflammatory cytokines, such as TNF-α and/or IL-12, comprising inflammatory diseases or auto-immune diseases. Diseases or conditions related to an excessive or unregulated production of proinflammatory cytokines comprise rheumatoid arthritis, rheumatoid spondylitis, spondyloarthropathies, systemic lupus erythematosus, osteoarthritis, gouty arthritis, juvenile arthritis and other arthritic conditions, polychondritis, sclerodoma, Wegener granulamatosis, dermatomyositis, Steven-Johnson syndrome, idiopathic sprue, endocrine opthalmopathy, Graves' disease, alveolitis, chronic hypersensitivity pneumonitis, primary billiary cirrhosis, uveitis, keratoconjunctivitis sicca and vernal keratoconjunctivitis, allergic rhinitis, pemphigus, eosinophilia, Loffler's syndrome, eosinophilic pneumonia, parasitic infestation, bronchopulmonary aspergillosis, polyarteritis nodosa, eosinophilic granuloma, eosinophil-related disorders affecting the airways occasioned by drug-reaction, sepsis, septic shock, endotoxic shock, gram negative sepsis, toxic shock syndrome, cerebral malaria, adult respiratory distress syndrome, bronchitis (acute, arachidic, catarrhal, chronic, croupus, phthinoid bronchitis), chronic obstructive airway or pulmonary disease, pulmonary fibrosis, tuberculosis, pneumoconiosis (aluminosis,anthracosis, asbestosis, chalicocis, ptilosis, siderosis, silicosis, tobaccosis, byssionosis), exacerbation of airways hyperreactivity to other drug therapy (e.g. aspirin or β-agonist therapy), silicosis, pulmonary sarcoidosis, bone resorption diseases, meningitis, allergic encephalitis, reperfusion injury, graft versus host reaction, allograft rejections, transplant rejections, fever and myalgias due to infection, such as influenza, cachexia (consequential to, e.g. bacterial, viral or parasitic, infection or to deprivation or deterioration of humoral or other organic function, or secondary to malignancy; malarial and vermal cachexia; cachexia resulting from dysfunction of the pituitary, thyroid or thymus glands as well as uremic cachexia; cachexia secondary to acquired immune deficiency syndrome (AIDS)), AIDS, ARC (AIDS related complex), diabetes, cancer, angiogenesis, lymphoma, Kawasaki syndrome, Behqet's syndrome, aphthous ulceration, skin-related disorders such as psoriasis, eczema, burns, dermatitis, keloid formation, scar tissue formation, erythema nodosum leprosum, Crohn's disease, ulcerative colitis, inflammatory bowel disease, irritable bowel syndrome, pyresis, asthma (intrinsic, extrinsic, allergic, non-atopic, exercise induced and occupational and bacterial infection induced asthma), wheezy infant syndrome, multiple sclerosis, Parkinson's disease, pancreatitis, cardiac disease, congestive heart failure, myocardial infarction, acute liver failure, glomerulonephritis, therapy-associated syndromes comprising Jarisch-Herxheimer reaction, and syndromes associated with IL-2 infusion, anti-CD3 antibody infusion, hemodialysis, yellow fever vaccination, HIV or other viral infections, such as Hepatitis C, CMV, influenza and herpes virus infections, pseudorabies and rhinotracheitis, angiofollicular lympoid hyperplasia, anemia (haemolytic, aplastic, pure red cell, idiopathic thrombocytopenia), neutropenia, lymphopenia, hepatosplenomegaly with mononuclear cell infiltration and pulmonary edema with interstitial cell infiltrates; or to prevent these diseases. In particular, the compounds of formula (I) or (I') can be used to treat rheumatoid arthritis, Crohn's disease, irritable bowel disease or colitis.

The cytokine production inhibitory activity of the compounds of formula (I) or (I') such as the inhibition of TNF-α and/or IL-12 production, may be demonstrated in the in vitro test "Inhibition of cytokine production in human whole blood cultures". Suitable in vivo tests are "Determination of cytokine in serum of LPS (lipopolysaccharide) and anti-CD3 challenged mice", "Inhibition of LPS-galactosamine induced shock in mice", "Inhibition of collagen induced arthritis in mice".

The compounds of formula (I) or (I') may also inhibit Interleukin-6 (IL-6).

The present compounds also have a selective affinity for adenosine $A_3$ receptors. Therefore, they can be used to prevent and/or treat adenosine related diseases such as asthma, allergosis, inflammation, Addison's disease, autoallergic hemolytic anemia, Crohn's disease, psoriasis, rheumatism, diabetes.

The present compounds may also act as intermediates for the preparation of further thiazolyl derivatives.

In view of the above described pharmacological properties, the compounds of formula (I) or (I') or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through cytokines, more in particular diseases mediated through TNF-α and/or IL-12, such as inflammatory and auto-immune diseases. The present compounds can also be used for the manufacture of a medicament for treating or preventing diseases mediated through activation of the adenosine $A_3$ receptor.

In view of the utility of the compounds of formula (I) or (I'), there is provided a method of treating warm-blooded animals, including humans, suffering from or a method of preventing warm-blooded animals, including humans, to suffer from diseases mediated through cytokines, in particular mediated through TNF-α and/or IL-12, such as inflammatory and auto-immune diseases. There is also provided a method of treating warm-blooded animals, including humans, suffering from or a method of preventing warm-blooded animals, including humans, to suffer from diseases mediated through activation of the adenosine $A_3$ receptor. Said methods comprise the administration, preferably oral administration, of an effective amount of a compound of formula (I) or (I'), a N-oxide form, a pharmaceutically acceptable addition salt, a quaternary amine or a possible stereoisomeric form thereof, to warm-blooded animals, including humans.

The present invention also provides compositions for preventing or treating diseases mediated through cytokines or mediated through activation of the adenosine $A_3$ receptor comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before ;use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated, β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-γ-CD, and in particular 2-hydroxypropyl-γ-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the through-put rate in the melt-extruder The water-soluble polymers in the particles are polymers that have an apparent viscosity, when dissolved at 20° C. in an aqueous solution at 2% (w/v), of 1 to 5000 mPa.s more preferably of 1 to 700 mPa.s, and most preferred of 1 to 100 mPa.s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β, or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxyC$_{2-4}$alkyl or carboxyC$_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl O-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between P-cyclodextrin an propylene oxide and may have a MS value of about 0.125 to 10, e.g. about 0.3 to 3.

Another type of substituted cyclodextrins is sulfobutyl-cyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of formula (I) may also be used in combination with other conventional anti-inflammatory or immunosuppressive agents, such as steroids, cyclooxygenase-2 inhibitors, non-steroidalanti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicaam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine, antilymphocytory immunoglobulines, antithymocytory immunoglobulines, azathioprine, cyclosporine, tacrolimus substances, ascomycin, rapamycin, muromonab-CD3.

Thus, the present invention also relates to the combination of a compound of formula (I) and another anti-inflammatory or immunosuppressive agent. Said combination may be used as a medicine. The present invention also relates to a product containing (a) a compound of formula (I), and (b) another anti-inflammatory or immunosuppressive compound, as a combined preparation for simultaneous, separate or sequential use in the treatment of diseases related to an excessive or unregulated cytokine production. The different drugs may be combined in a single preparation together with pharmaceutically acceptable carriers.

Experimental Part

A. Preparation of the Intermediate Compounds

EXAMPLE A1

2-Bromo-acetoacetaldehyde (0.1 mol) was added portionwise to pyrazinamine (0.1 mol) in ethanol (200 ml) while stirring. The reaction mixture was stirred and refluxed for one hour, then allowed to cool to room temperature. The precipitate was filtered off and dried. Yield: 13.5 g of 1-(imidazo[1,2-a]pyrazin-3-yl)ethanone (55%) (interm. 1).

EXAMPLE A2 a) A mixture of 2-pyrimidinamine (0.5 mol) and 1,1-dimethoxy-N,N-dimethyl-methanamine (0.55 mol) in methylbenzene (500 ml) was stirred and refluxed for 2 hours. The reaction mixture was cooled and the solvent was evaporated. Yield: ±75 g of N,N-dimethyl-N'-(2-pyrimidinyl)methanimidamide (interm. 2). b) A mixture of intermediate (2) (0.066 mol) and 1-chloro-2-propanone (0.13 mol) in CH$_2$Cl$_2$ (500 ml) was stirred and refluxed for 48 hours. The reaction mixture was cooled and the solvent was evaporated. The residue was crystallized from CH$_3$CN, filtered off, washed and dried. Yield: 6.9 g of imidazo[1,2-a]pyrimidin-3-ylethanone (65.1%) (interm. 3).

EXAMPLE A3 a) A mixture of 6-(trifluoromethyl)-3-pyridinecarboxylic acid (0.026 mol) in thionyl chloride (50 ml) was stirred and refluxed for 2 hours. The solvent was evaporated. Yield: 5.2 g of 6-(trifluoromethyl)-3-pyridinecarbonyl chloride (interm. 4)

b) A mixture of 2,2-dimethyl-1,3-dioxane-4,6-dione (0.025 mol) in dichloromethane (150 ml) was stirred under N$_2$ flow and cooled to 0° C. N,N-Dimethyl-4-pyridinamine (0.055 mol) was dissolved in dichloromethane (50 ml) and added dropwise to the first solution at 0° C. This reaction mixture was stirred for 30 minutes without an ice-bath. The mixture was again cooled and intermediate 4 (0.025 mol) was dissolved in dichloromethane (100 ml) and added dropwise to the first solution at 0° C. The reaction mixture was stirred for 2 hours at 0° C. and overnight at room temperature under N$_2$ flow. The solvent was evaporated and the residue was taken up in ethyl acetate and washed with HCl 1N (30 ml) and H$_2$O (70 ml) and again with H$_2$O (2×). The separated organic layer was dried, filtered and the solvent was evaporated. Yield : 6.1 g of 1-[6-(trifluoromethyl)-3-pyridinyl]ethanone (interm. 5)

EXAMPLE A4

Reference method: Lipinski et al. J.Org.Chem. 1984,49, 50. A solution of acetyl chloride (0.072 mol) in dichloromethane (10 ml) was added dropwise to a mixture of 1-(2-methyl-1H-imidazol-4-yl)ethanone (0.024 mol) and N,N-diethylethanamine (0.072 mol) in dichloromethane (230 ml). The mixture was stirred for 1 hour. N,N-diethylethanamine (0.75 g) was added again. The mixture was washed very shortly with ice water (50 ml) and separated into its layers. The aqueous layer was extracted twice with CH$_2$Cl$_2$ (30 ml). The combined organic layer was dried (MgSO$_4$), filtered and the solvent was evaporated. The residue was dissolved in CH$_2$Cl$_2$ (100 ml). trimethyloxonium tetrafluoroborate (0.053 mol) was added. Na$_2$CO$_3$ (80 nml) was added. The organic layer was separated, dried (MgSO4), filtered and the solvent was evaporated. The residue was purified by column chromatography over silica gel (eluent: CH$_2$Cl$_2$/CH$_3$OH 100/0 to 98/2). The pure fractions were collected and the solvent was evaporated. Yield: 3.4 g of 1-(1,2-dimethyl-1-H-imidazol-5-yl)ethanone (interm. 6)

EXAMPLE A5 a) 6-Chloro-imidazo[1,2-a]pyridine (0.1 mol) was dissolved in CS$_2$ (400 ml). The solution was warmed. AlCl$_3$ (0.3 mol) was added portionwise (exothermic temperature rise to reflux temperature). A solution of chloroacetyl chloride (0.2 mol) in CS$_2$ (100 ml) was added dropwise and the reaction mixture was stirred and refluxed for 4 hours, then stirred overnight at room temperature. The mixture was decomposed with ice (200 g). CH$_3$OH (100 ml) was added. 1N HCl (100 ml) was added and the mixture was stirred for 2 hours. The precipitate was filtered off, rinsed with 2-propanone and dried. Yield: 8.86 g of 2-chloro-1-(6-chloroimidazo[1,2-a]pyridin-3-yl)ethanone monohydrochloride (interm. 7). The filtrate was alkalized with Na$_2$CO$_3$, then with 50% NaOH. This mixture was extracted with ethyl acetate (3×). The separated organic layer was dried, filtered and the solvent evaporated. The residue was dissolved in 2-propanone and converted into the hydrochloric acid salt (1:1) with HCl/2-propanol. The precipitate was filtered off and dried. Yield: 1.81 g of intermediate (7). Total yield: 10.67 g (40.2%) of intermediate (7).

b) Reaction under N$_2$ atmosphere. Tetrahydrofuran (700 ml) was cooled to −70° C. n-Butyllithium 2.5M in hexane (100 ml) was added. A solution of N-(1-methylethyl)-2-propanamine (0.22 mol) in tetrahydrofuran (100 ml) was added dropwise at −70° C., then warmed slowly to −40° C. and stirred for 30 minutes at 40° C. The reaction mixture was re-cooled to −70° C. A solution of imidazo[1,5-a]pyridine (0.2 mol) in tetrahydrofuran (100 ml) was added dropwise and the reaction mixture was stirred for 2 hours, allowing the temperature to rise to ±−30° C. The reaction mixture was re-cooled to −70° C. A solution of N,N-dimethyl-2-chloroacetamide (0.22 mol) in tetrahydrofuran (100 ml) was added dropwise. The cooling bath was removed and the reaction mixture was stirred until the temperature reached ±0° C. The reaction mixture was cooled, decomposed with ice and 2N HCl. The layers were separated. The water layer was extracted twice with ethyl acetate. The separated organic layer was dried, filtered and the solvent evaporated. Yield: 24 g of 2-chloro-1-(imidazo[1,5-a]pyridin-3-yl)ethanone (62%) (interm. 8).

c) Intermediate (1) (0.02 mol) in HBr 48% (90 ml) was stirred at 70° C. A solution of Br$_2$ (0.02 mol) in HBr 48% (10 ml) was added dropwise and the reaction mixture was stirred for one hour at 70° C. The solvent was evaporated. The residue was stirred in 2-propanone with a small amount of ethanol, filtered off and dried. Yield: 6.15 g of 2-bromo-1-(imidazo[1,2-a]pyrazin-3-yl)ethanone monohydrobromide (interm. 9).

d) 1-(1H-indazol-3-yl)ethanone (0.01 mol) was stirred in 1,4-dioxane (100 ml), at room temperature. A solution of Br$_2$ (0.01 mol) in 1,4-dioxane (20 ml) was added dropwise and the resulting reaction mixture was stirred overnight at room temperature. The precipitate was filtered off and the filtrate was evaporated. The residue was crystallized from CH$_3$OH, filtered off and dried. Yield: 0.73 g of 2-bromo-1-(1H-indazol-3-yl)ethanone (interm. 10).

e) Intermediate (3) (0.15 mol) was dissolved in acetic acid (250 ml). A solution of Br$_2$ (0.3 mol) in acetic acid (40 ml) was added dropwise at room temperature and the resulting reaction mixture was stirred for 2 hours at 100° C. (steam bath). The reaction mixture was cooled to 0° C., then stirred overnight at room temperature. The precipitate was filtered off, washed and dried (in vacuo). Yield: 40.4 g (84.2%, mixture of two major compounds). HPLC separation gave two fraction groups. The solvent of each group was evaporated. Yield: 17 g of 2,2-dibromo-1-(imidazo[1,2-a]pyrimidin-3-yl)ethanone (interm. 8) and 7.2 g of 2-bromo-1-(imidazo[1,2-a]-pyrimidin-3-yl)ethanone monohydrobromide (interm. 11).

f) 1-(6-chloroimidazo[1,2-b]pyridazin-3-yl)ethanone (0.005 mol) was dissolved in a solution of hydrobromide 48% (15 ml). The mixture was heated to ±70° C. Br$_2$ (0.005 mol) was added dropwise over 15 minutes. The reaction mixture was stirred overnight at room temperature. The precipitate was filtered off, washed, then suspended in 2-propanone. The precipitate was filtered off, washed and dried. Yield: 1.2 g of 2,2-dibromo-1-(6-chloroimidazo[1,2-b]pyridazin-3-yl)ethanone (interm. 12).

EXAMPLE A6 a) N,N-diethylethanamine (2.61 g) was added to a mixture of 6-(trifluoromethyl)-3-pyridinecarboxylic acid (0.025 mol) in t-butanol (100 ml). The mixture was warmed up to 90° C. Phosphorazidic acid, diphenyl ester (0.025 mol) was added dropwise ($N_2$-development). The mixture was stirred at 90° C. overnight. The solvent was evaporated. The residue (16.98 g) was purified by column chromatography over silica gel (eluent $CH_2Cl_2$ 100%). The pure fractions were collected and the solvent was evaporated. Yield: 6.3 g (96%) of carbamic acid, (6-trifluoromethyl-3-pyridinyl), 1,1-dimethylethyl ester (interm. 13)

b) HBr/acetic acid (30 ml) was added to a mixture of intermediate 13 (0.02 mol) and ethyl acetate (150 ml) (a precipitate was formed immediately). EtOH was added. More HBr/acetic acid (10 ml) was added. The solvent was evaporated. The residue was taken up in ethyl acetate. NaOH (1M) was added. The mixture was extracted. The organic layer was separated, dried, filtered and the solvent was evaporated. HCl 1M (100 ml) was added. The solution was stirred at 80° C. for 4 hours. The solvent was evaporated. NaOH (1M) was added. The mixture was extracted with $CH_2Cl_2$ (3×100 ml). The combined organic layer was dried, filtered and the solvent was evaporated. Yield: 2.64 g of 6-(trifluoromethyl)-3-pyridinamine (interm. 14).

c) A solution of benzoyl isothiocyanate (0.016 mol) in tetrahydrofuran (50 ml) was added at room temperature to a mixture of intermediate 14 (0.016 mol) in tetrahydrofuran (200 ml). The mixture was stirred overnight. The solvent was evaporated. The residue was stirred in diisopropyl ether. The precipitate was filtered off and dried in vacuo at 40° C. Yield: 3.189 g (61.3%) of N-[[6-(trifluoromethyl)-3-pyridinyl-amino]thioxomethyl]benzamide (interm. 15).

d) A mixture of intermediate 15 (0.0098 mol) and NaOH 1M (0.01 mol) in ethanol (150 ml) was stirred and refluxed for 30 minutes and then cooled. $MgSO_4$ was added. The mixture was filtered and the filtrate was evaporated. The residue was stirred in diisopropyl ether, stirred and refluxed, cooled, filtered and dried. Yield: 1.178 g (54.3%) of [6-(trifluoromethyl)-3-pyridinyl] thiourea (interm. 16).

The following intermediates were prepared analogous to one of the above examples (the example number according to which they were prepared is indicated between square brackets after the intermediate number).

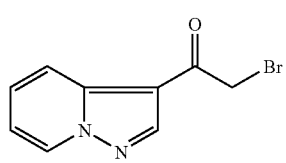

interm. 17 [A5d]

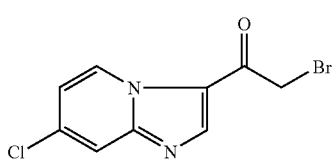

interm. 18 [A5c]

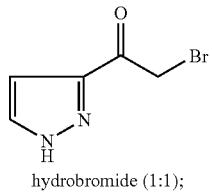

interm. 19 [A5c]

hydrobromide (1:1);

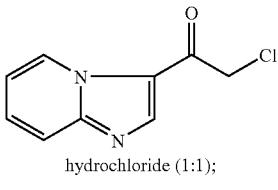

interm. 20 [A5a]

hydrochloride (1:1);

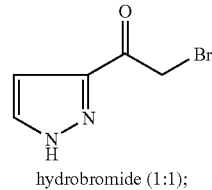

interm. 21 [A1]

hydrobromide (1:1);

B. Preparation of the Final Compounds

EXAMPLE B1 a) A mixture of 2-chloro-1-(imidazo[2,1-b]thiazol-5-yl) ethanone monohydrochloride (0.0025 mol), prepared according to A5a), and intermediate 16 (0.0025 mol) in ethanol (50 ml) was stirred at 80° C. for 10 hours and then cooled. The precipitate was filtered off and dried. Yield: 0.54 g of 4-(imidazo[2,1-b]thiazol-5-yl)-N-[(6-trifluoromethyl)-3-pyridinyl]-2-thiazolamine monohydrochloride; mp 242° C. (comp. 568).

(b) A mixture of intermediate (10) (0.001 mol) and (4-chlorophenyl)thiourea (0.001 mol) in ethanol (10 ml) was stirred for 3 hours at ±70° C., then stirred overnight at room temperature. The precipitate was filtered off and dried. Yield: 0.33 g of N-(4-chloro-phenyl)-4-imidazo[1,2-a]pyrazin-3-yl-2-thiazolamine monohydrobromide (comp. 2).

c) A mixture of intermediate (11) (0.005 mol) and 3-pyridinylthiourea (0.005 mol) in ethanol (50 ml) was stirred and refluxed for 12 hours, then cooled and the resulting precipitate was filtered off, washed and dried (vacuum). Yield: 0.2 g of N-(4-imidazo-[1,2-a]pyrimidin-3-yl-2-thiazolyl)-3-pyridinamine monohydrobromide (10.5%) (comp. 3).

d) A mixture of 2-bromo 1-(5-methyl-3-pyridinyl)ethanone (0.00125 mol) and 2,2-dibromo 1-(5-methyl-3-pyridinyl)ethanone (0.00125 mol), both prepared according to, A5e), and [3-(trifluoromethyl)-phenyl]thiourea in ethanol (25 ml) was stirred and 35, refluxed for 3 hours. The reaction mixture was stirred overnight at room temperature A solid was formed, filtered off, washed and dried (vacuum). Yield: 0.4 g of N-[3-(trifluoromethyl)phenyl]-4-[5-methyl-3-pyridinyl]-2-thiazolamine monohydrobromide (comp. 626).

EXAMPLE B2

A mixture of N-(3-nitro-phenyl4-imidazo[1,2-a]pyridin-3-yl-2-thiazolamine, (0.003 mol), prepared according to the synthesis procedure described under B1a-2), in methanol (150 ml) was hydrogenated with palladium-on-charcoal 10% (1 g) as a catalyst in the presence of thiophene 4% in diisopropylether (1 ml). After uptake of hydrogen (3 equivalents), the catalyst was filtered off and the filtrate was evaporated. The residue was dissolved in ethanol and converted into the hydrochloric acid salt (1:2) with HCl/2-propanol. The precipitate was filtered off and dried. Yield: 0.85 g of N-(4-imidazo[1,2-a]pyridin-3-yl-2-thiazolyl)-1,3-benzenediamine dihydrochloride monohydrate (comp 5).

EXAMPLE B3

A mixture of compound (6) (see Table 2) (0.0025 mol), prepared according to the synthesis procedure described under B1b), in HCl conc. (10 ml) and water (10 ml) was stirred and refluxed for 1 hour. HCl conc. (10 ml) and water (10 ml) were added again. The mixture was stirred and refluxed for 16 hours. The solvent was evaporated. The residue was crystallized from $CH_3OH$. The precipitate was filtered off and dried in vacuo at 50° C. for 16 hours. Yielding: 0.4 g of 4-[(4-imidazo[1,2-a]pyridin-3-yl-2-thiazolyl)amino]benzoic acid monohydrochloride (38%) (comp. 7).

EXAMPLE B4

A mixture of compound 634 (0.0014 mol) in water (60 ml) was stirred and then a hydrobromide solution 48% (6 ml) was added. The reaction mixture was stirred and refluxed for 8 hours. The reaction mixture was stirred further for 48 hours at room temperature under $N_2$ flow. The solvent is evaporated. The residue was crystallized from 2-propanone and $CH_3CN$. The precipitate was filtered off and dried. Yield: 0.61 g of 6-[2-[[2,3-dichlorophenyl]amino]-4-thiazolyl]pyridinamine monohydrobromide; mp. 236° C. (comp. 635).

EXAMPLE B5

A mixture of N-[5-[(1-oxo-2-bromo)ethyl]-2-pyridinyl]acetamide (0.002 mol), prepared according to A5c), and [3-(trifluoromethyl)phenyl]thiourea (0.002 mol) in ethanol (100 ml) was stirred and refluxed for 1 hour. The mixture was cooled and the precipitate was filtered off. This precipitate was stirred in water (90 ml) and a hydrobromide solution 48% (10 ml) was added dropwise. The reaction mixture was stirred and refluxed overnight, cooled off and washed with $CH_2Cl_2$ (2×). The aqueous layer was evaporated until dry, stirred in 2-propanone, filtered off and dried. The precipate was stirred in water and the formed precipitate was filtered off and dried. Yeild 0.25 g of 6-[2-[[3-(trifluoromethyl)phenyl]amino]4-thiazolyl]pyridinamine monhydrobromide monohydrate; mp. 148° C. (comp. 637). Tables 1 to 12 list the compounds of formula (I) which were prepared according to one of the above described examples.

TABLE 1

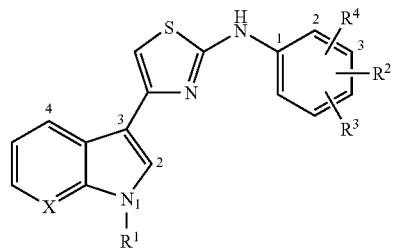

| Co. no. | Ex. no. | X | $R^1$ | $R^2$ | $R^3$ | $R^4$ | Physical data |
|---|---|---|---|---|---|---|---|
| 8 | B1a | CH | H | 4-$OCH_3$ | H | H | HCl (1:1); mp. 235° C. |
| 9 | B1a | CH | H | H | H | H | HCl (1:1); mp. 170–172° C. (dec)* |
| 10 | B1a | N | H | 4-$OCH_3$ | H | H | HCl (1:2); mp. 222° C. |
| 11 | B1a | N | H | H | H | H | HCl (1:2); $H_2O$ (1:1); mp. 188° C. |
| 12 | B1a | N | H | 3-$CF_3$ | H | H | HCl (1:2); mp. 190° C. |
| 13 | B1a | N | H | 4-$CH_3$ | H | H | HCl (1:2); mp. 210° C. |
| 14 | B1a | N | H | 3-$CH_3$ | H | H | HCl (1:2); mp. 198° C. |
| 15 | B1a | N | H | 3-$OCH_3$ | H | H | HCl (1:2); mp. 198° C. |
| 16 | B1a | N | H | 4-$CF_3$ | H | H | HCl (1:1); mp. 228° C. |
| 17 | B1a | CH | $CH_3$ | H | H | H | HCl (1:1) |
| 18 | B1a | CH | $CH_3$ | 4-$OCH_3$ | H | H | HCl (1:1) |
| 19 | B1a | N | H | 4-$COOC_2H_5$ | H | H | HCl (1:2) |
| 20 | B1a | N | H | 4-Br | H | H | HCl (1:2) |
| 22 | B1a | CH | H | 4-$CH_3$ | H | H | HCl (1:1); $H_2O$ (1:1) |
| 48 | B1a | N | H | 2-F | 3-F | 4-F | HCl (1:2) |
| 151 | B1a | N | H | 2-$CF_3$ | H | H | HCl (1:2) |
| 152 | B1a | N | H | 4-$OCH_2$-phenyl | H | H | HCl (1:2) |
| 153 | B1a | N | H | 3-Br | H | H | HCl (1:2) |
| 154 | B1a | N | H | 2-$OCF_3$ | H | H | HCl (1:2) |
| 155 | B1a | N | H | 2-$CH(CH_3)_2$ | H | H | HCl (1:2) |
| 156 | B1a | N | H | 2-$SCH_3$ | H | H | HCl (1:2) |
| 157 | B1a | N | H | 2-$OC_2H_5$ | H | H | HCl (1:2) |
| 158 | B1a | N | H | 2-$CH_3$ | H | H | HCl (1:2) |
| 159 | B1a | N | H | 2-F | H | H | HCl (1:2) |

TABLE 1-continued

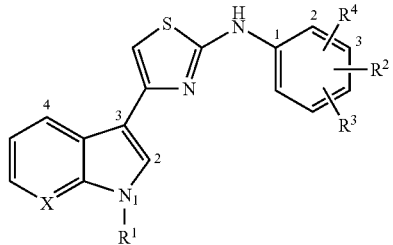

| Co. no. | Ex. no. | X | R¹ | R² | R³ | R⁴ | Physical data |
|---|---|---|---|---|---|---|---|
| 160 | B1a | N | H | 3-Cl | 4-Br | H | HCl (1:2) |
| 161 | B1a | N | H | 4-CF₃ | 2-Cl | H | HCl (1:2) |
| 162 | B1a | N | H | 4-CH₃ | 3-Cl | H | HCl (1:2) |
| 163 | B1a | N | H | 2-CH₃ | 4-Cl | H | HCl (1:2) |
| 164 | B1a | N | H | 3-F | 4-F | H | HCl (1:2) |
| 165 | B1a | N | H | 2-CH₃ | 3-Cl | H | HCl (1:2) |
| 166 | B1a | N | H | 2-Cl | 3-Cl | H | HCl (1:2); mp. 227–229° C. (dec)* |
| 168 | B1a | N | H | 2-CH₃ | 5-Cl | H | HCl (1:2) |
| 169 | B1a | N | H | 2-CH₃ | 5-F | H | HCl (1:2) |
| 170 | B1a | N | H | 2-CH₃ | 4-CH₃ | 5-CH₃ | HCl (1:2) |
| 171 | B1a | N | H | 2-OCH₃ | 4-Cl | 5-OCH₃ | HCl (1:2) |
| 172 | B1a | N | H | 2-Cl | 4-Cl | 5-Cl | HCl (1:2) |
| 173 | B1a | N | H | 3-OCH₃ | 4-OCH₃ | 5-OCH₃ | HCl (1:2) |
| 174 | B1a | N | H | 2-Cl | 5-CF₃ | H | HCl (1:2) |
| 175 | B1a | N | H | 2-OCH₃ | 5-Cl | H | HCl (1:2) |
| 176 | B1a | N | H | 2-OCH₃ | 5-CH₃ | H | HCl (1:2) |
| 177 | B1a | N | H | 2-OCH₃ | 5-OCH₃ | H | HCl (1:2) |
| 178 | B1a | N | H | 3-Cl | 5-Cl | H | HCl (1:2) |
| 179 | B1a | N | H | 2-CH₃ | 3-CH₃ | H | HCl (1:2) |
| 180 | B1a | N | H | 3-CH₃ | 5-CH₃ | H | HCl (1:2) |
| 181 | B1a | N | H | 2-OCH₃ | 4-OCH₃ | H | HCl (1:2) |
| 182 | B1a | N | H | 3-CF₃ | 4-Cl | H | HCl (1:2) |
| 183 | B1a | N | H | 2-Br | 4-CH₃ | H | HCl (1:2) |
| 184 | B1a | N | H | 2-CH₃ | 4-CH₃ | H | HCl (1:2) |
| 185 | B1a | N | H | 2-CF₃ | 4-Br | H | HCl (1:2) |
| 187 | B1a | N | H | 2-OCH₃ | H | H | HCl (1:2) |
| 188 | B1a | N | H | 2-OH | H | H | HCl (1:2) |
| 189 | B1a | N | H | 2-Cl | H | H | HCl (1:2) |
| 190 | B1a | N | H | 2-Br | H | H | HCl (1:2) |
| 191 | B1a | N | H | 3-SCH₃ | H | H | HCl (1:2) |
| 192 | B1a | N | H | 3-OH | H | H | HCl (1:2) |
| 193 | B1a | N | H | 3-F | H | H | HCl (1:2) |
| 194 | B1a | N | H | 3-CN | H | H | HCl (1:2) |
| 195 | B1a | N | H | 4-O-phenyl | H | H | HCl (1:2) |
| 196 | B1a | N | H | 2-(2,4-dichlo-rophenoxy) | H | H | HCl (1:2) |
| 197 | B1a | N | H | 2-F | 5-F | H | HCl (1:2) |
| 198 | B1a | N | H | 2-F | 4-F | H | HCl (1:2) |
| 199 | B1a | N | H | 2-Cl | 4-Cl | H | HCl (1:2) |
| 200 | B1a | N | H | 3-Cl | 4-Cl | H | HCl (1:2) |
| 203 | B1a | N | H | 2-C₂H₅ | H | H | HCl (1:2) |
| 204 | B1a | N | H | 3-COOH | H | H | HCl (1:2) |
| 205 | B1a | N | H | 3-COOC₂H₅ | H | H | HCl (1:2) |
| 206 | B1a | N | H | 3-COCH₃ | H | H | HCl (1:2) |
| 207 | B1a | N | H | 4-OH | H | H | HCl (1:2) |
| 208 | B1a | N | H | 4-OC₂H₅ | H | H | HCl (1:2) |
| 209 | B1a | N | H | 4-OCF₃ | H | H | HCl (1:2) |
| 211 | B1a | N | H | 4-F | H | H | HCl (1:2) |
| 212 | B1a | N | H | 4-cyclohexyl | H | H | HCl (1:2) |
| 213 | B1a | N | H | 4-CN | H | H | HCl (1:2) |
| 214 | B1a | N | H | 4-C₂H₅ | H | H | HCl (1:2) |
| 215 | B1a | N | H | 4-COOH | H | H | HCl (1:2) |
| 217 | B1a | N | H | 3-Cl | H | H | HCl (1:2) |
| 21 | B1a | N | H | 2-Cl | 5-Cl | H | HCl (1:2) |
| 186 | B1a | N | H | 3-CF₃ | 5-CF₃ | H | HCl (1:2) |
| 210 | B1a | N | H | 3-S(O)₂—NH₂ | H | H | HCl (1:1) |

*= decomposition

TABLE 2

| Co. no. | Ex. no. | R¹ | R² | R³ | R⁴ | Physical data |
|---|---|---|---|---|---|---|
| 1 | B1a | 6-Cl | 4-OCH₃ | H | H | HCl (1:1) |
| 23 | B1a | H | 4-OCF₃ | H | H | HCl (1:1); mp. 222° C. |
| 24 | B1a | H | 3-Cl | H | H | HCl (1:1) |
| 25 | B1a | H | 2-Cl | H | H | HCl (1:1); H₂O (1:1) |
| 26 | B1a | H | 3-COOH | H | H | HCl (1:1) |
| 27 | B1a | H | 3-COOC₂H₅ | H | H | HCl (1:1) |
| 28 | B1a | H | 2-OCH₃ | 4-OCH₃ | H | HCl (1:1); mp. 158° C. |
| 29 | B1a | H | 3-OCH₃ | H | H | HCl (1:1) |
| 30 | B1a | H | 3-Cl | 5-Cl | H | HCl (1:1) |
| 31 | B1a | H | 3-CH₃ | H | H | HCl (1:1); mp. 218–220° C. (dec)* |
| 32 | B1a | H | 4-OC₂H₅ | H | H | HCl (1:1) |
| 33 | B1a | H | 3-S—CH₃ | H | H | HCl (1:1); mp. 220° C. |
| 34 | B1a | H | 2-OCH₃ | H | H | HCl (1:1); ethanolate (1:1); mp. 152° C. |
| 35 | B1a | H | 3-OH | H | H | HCl (1:1) |
| 36 | B1a | H | 3-COCH₃ | H | H | HCl (1:1) |
| 37 | B1a | H | 4-Cl | H | H | HCl (1:1); ethanolate (1:1) |
| 38 | B1a | H | 3-CF₃ | 4-Cl | H | HCl (1:1) |
| 39 | B1a | H | 4-CH₃ | H | H | HCl (1:1); mp. >250° C. |
| 40 | B1a | H | 2-OH | H | H | HCl (1:2) |
| 41 | B1a | H | 2-S—CH₃ | H | H | HCl (1:2); ethanolate (1:1) |
| 42 | B1a | H | 4-I | H | H | HCl (1:1) |
| 43 | B1a | H | 3-Cl | 4-Cl | H | HCl (1:1); mp. >260° C. |
| 44 | B1a | H | 4-COOC₂H₅ | H | H | HCl (1:1) |
| 45 | B1a | H | 2-Cl | 3-Cl | H | HCl (1:1), H₂O (1:1); mp. 150–154° C. (dec)* |
| 46 | B1a | H | 2-F | 3-F | 4-F | HCl (1:1) |
| 47 | B1a | H | 3-CH₃ | 5-CH₃ | H | HCl (1:1) |
| 52 | B1a | H | 4-cyclohexyl | H | H | HCl (1:1) |
| 54 | B1a | 6-Cl | 4-CH₃ | H | H | HCl (1:1); mp. 232° C. |
| 55 | B1a | 6-Cl | 3-CF₃ | H | H | HCl (1:1); H₂O (1:1); mp. 222° C. |
| 56 | B1a | 6-Cl | 3-OH | H | H | HCl (1:1) |
| 57 | B1a | H | 4-CH(CH₃)₂ | H | H | HCl (1:1) |
| 58 | B1a | H | 2-Cl | 4-Cl | 6-Cl | HCl (1:1) |
| 59 | B1a | H | 2-Cl | 6-Cl | H | |
| 60 | B1a | H | 2-CH₃ | 6-CH₃ | H | |
| 61 | B1b | 2-CH₃ | 4-OCH₃ | H | H | |
| 62 | B1b | 2-CH₃ | H | H | H | mp. 221–223° C. |
| 63 | B1b | 2-CH₃ | 2-CH₃ | H | H | HBr (1:1); mp. 190° C. |
| 64 | B1b | 2-CH₃ | 4-CH₃ | H | H | HBr (1:1); ethanolate (1:1); mp. >260° C. |
| 65 | B1b | 2-CH₃ | 2-F | H | H | HBr (1:1); mp. 246° C. |
| 66 | B1b | 2-CH₃ | 3-F | H | H | HBr (1:1) |
| 67 | B1b | 2-CH₃ | 4-F | H | H | HBr (1:1); mp. >258° C. |
| 68 | B1b | 2-CH₃ | 3-CN | H | H | HBr (1:1) |
| 69 | B1b | 2-CH₃ | 4-CN | H | H | HBr (1:1); mp. >260° C. |
| 70 | B1b | 2-CH₃ | 2-OCH₃ | H | H | HBr (1:1); mp. 204° C. |
| 71 | B1b | 2-CH₃ | 4-OH | H | H | HBr (1:1); mp. >260° C. |
| 72 | B1b | 2-CH₃ | 2-CF₃ | H | H | HBr (1:1); mp. 250° C. |
| 73 | B1b | 2-CH₃ | 2-OCF₃ | H | H | HBr (1:1) |
| 74 | B1b | H | 4-OCH₃ | H | H | HBr (1:1); mp. 254° C. |
| 75 | B1b | H | 4-CH₃ | H | H | HBr (1:1); mp. >260° C. |
| 76 | B1b | 2-CH₃ | 3-CF₃ | H | H | HBr (1:1); mp. 256° C. |
| 77 | B1b | 2-CH₃ | 4-OCF₃ | H | H | HBr (1:1) |
| 78 | B1b | 2-CH₃ | 4-CF₃ | H | H | HBr (1:1); ethanolate(1:1) |
| 79 | B1b | H | 2-F | H | H | HBr (1:1) |
| 80 | B1b | H | H | H | H | HBr (1:1) |
| 81 | B1b | H | 3-CF₃ | H | H | HBr (1:1); mp. 260–262° C. (dec)* |

TABLE 2-continued

| Co. no. | Ex. no. | R$^1$ | R$^2$ | R$^3$ | R$^4$ | Physical data |
|---|---|---|---|---|---|---|
| 82 | B1b | H | 4-CF$_3$ | H | H | HBr (1:1); mp. 260–262° C. (dec)* |
| 83 | B1b | H | 4-OH | H | H | HBr (1:1), mp. >260° C. |
| 84 | B1b | 2-CH$_3$ | 4-S—CH$_3$ | H | H | HBr (1:1) |
| 85 | B1b | H | 4-S—CH$_3$ | H | H | HBr (1:1) |
| 86 | B1b | H | 4-C$_2$H$_5$ | H | H | HBr (1:1); mp. >260° C. |
| 87 | B1b | 2-CH$_3$ | 4-C$_2$H$_5$ | H | H | HBr (1:1); mp. 238° C. |
| 90 | B1b | H | 4-F | H | H | |
| 92 | B1b | H | 3-CN | H | H | HCl (1:1) |
| 6 | B1b | H | 4-CN | H | H | HBr (1:1) |
| 99 | B1b | 2-CH$_3$ | 2-Cl | H | H | HBr (1:1) |
| 104 | B1b | 2-CH$_3$ | 3-Cl | H | H | HBr (1:1) |
| 105 | B1b | H | 3-CF$_3$ | 5-CF$_3$ | H | |
| 107 | B1b | H | 2-OCF$_3$ | H | H | HBr (1:1); mp. >250° C. |
| 124 | B1b | 7-Cl | 4-OCH$_3$ | H | H | HBr (1:1) |
| 5 | B2 | H | 3-NH$_2$ | H | H | HCl (1:2); H$_2$O (1:1) |
| 7 | B3 | H | 4-COOH | H | H | HCl (1:1) |
| 134 | B1b | 2-CH$_3$ | 4-OCH$_3$ | H | H | HBr (1:2) |
| 135 | B1b | 2-CH$_3$ | 4-Br | H | H | HBr (1:1) |
| 136 | B1b | 2-CH$_3$ | 3-CH$_3$ | H | H | HBr (1:1) |
| 137 | B1c | 2-CH$_3$ | 4-N(CH$_3$)$_2$ | H | H | HBr (1:1) |
| 138 | B1b | 2-CH$_3$ | 4-[methylsulfonamido-5-methylisoxazole] | H | H | HBr (1:1); H$_2$O (1:1) |
| 139 | B1c | 2-CH$_3$ | 4-NH$_2$ | H | H | HBr (1:1) |
| 141 | B1b | 2-CH$_3$ | 4-NH—CO—CH$_3$ | H | H | HBr (1:1) |
| 142 | B1b | 2-CH$_3$ | 3-OH | H | H | HBr (1:1) |
| 144 | B1b | 2-CH$_3$ | 4-[methylsulfonamido-2,6-dimethoxypyrimidine] | H | H | HBr (1:1) |
| 465 | B1a | H | 4-OCH$_2$-phenyl | H | H | HCl (1:1) |
| 466 | B1a | H | 3-Br | H | H | |
| 467 | B1a | H | 2-OCF$_3$ | H | H | HCl (1:1) |
| 468 | B1a | H | 2-CH(CH$_3$)$_2$ | H | H | HCl (1:1) |
| 469 | B1a | H | 2-SCH$_3$ | H | H | HCl (1:1) |
| 470 | B1a | H | 2-OC$_2$H$_5$ | H | H | HCl (1:1) |
| 471 | B1a | H | 2-CH$_3$ | H | H | HCl (1:1) |
| 472 | B1a | H | 2-F | H | H | HCl (1:1) |
| 473 | B1a | H | 2-CF$_3$ | H | H | HCl (1:1) |
| 474 | B1a | H | 3-Cl | 4-Br | H | HCl (1:1) |
| 475 | B1a | H | 2-Cl | 4-CF$_3$ | H | HCl (1:1) |
| 476 | B1a | H | 3-Cl | 4-CH$_3$ | H | HCl (1:1) |
| 477 | B1a | H | 2-CH$_3$ | 4-Cl | H | HCl (1:1) |
| 478 | B1a | H | 3-F | 4-F | H | HCl (1:1) |
| 479 | B1a | H | 2-CH$_3$ | 3-Cl | H | HCl (1:1) |
| 481 | B1a | H | 2-CH$_3$ | 5-Cl | H | HCl (1:1) |
| 482 | B1a | H | 2-CH$_3$ | 5-F | H | HCl (1:1) |
| 483 | B1a | H | 2-CH$_3$ | 4-CH$_3$ | 5-CH$_3$ | HCl (1:1) |
| 484 | B1a | H | 2-OCH$_3$ | 4-Cl | 5-OCH$_3$ | HCl (1:1) |
| 485 | B1a | H | 2-Cl | 4-Cl | 5-Cl | HCl (1:1) |

TABLE 2-continued

| Co. no. | Ex. no. | R¹ | R² | R³ | R⁴ | Physical data |
|---|---|---|---|---|---|---|
| 486 | B1a | H | 3-OCH₃ | 4-OCH₃ | 5-OCH₃ | HCl (1:1) |
| 488 | B1a | H | 2-Cl | 5-CF₃ | H | HCl (1:1) |
| 489 | B1a | H | 2-OCH₃ | 5-Cl | H | HC1(1:1) |
| 490 | B1a | H | 2-OCH₃ | 5-CH₃ | H | HCl (1:1) |
| 491 | B1a | H | 2-OCH₃ | 5-OCH₃ | H | HCl (1:1) |
| 492 | B1a | H | 2-CH₃ | 3-CH₃ | H | HCl (1:1) |
| 494 | B1a | H | 2-Br | 4-CH₃ | H | HCl (1:1) |
| 495 | B1a | H | 2-CH₃ | 4-CH₃ | H | HCl (1:1) |
| 496 | B1a | H | 2-CF₃ | 4-Br | H | HCl (1:1) |
| 498 | B1a | H | 2-Br | H | H | HCl (1:1) |
| 499 | B1a | H | 3-F | H | H | HC1(1:1) |
| 500 | B1a | H | 3-CN | H | H | HCl (1:1) |
| 501 | B1a | H | 4-phenoxy | H | H | HCl (1:1) |
| 502 | B1a | H | 2-C₂H₅ | H | H | HCl (1:1) |
| 504 | B1a | H | 2-Cl | 4-Cl | H | HCl (1:1) |
| 505 | B1a | H | 2-F | 4-F | H | HCl (1:1) |
| 506 | B1a | H | 2-Cl | 5-Cl | H | HCl (1:1) |
| 507 | B1a | H | 2-F | 5-F | H | HCl (1:1) |
| 508 | B1a | H | 2-(2,4-dichlorophenoxy) | H | H | HCl (1:1) |
| 509 | B1a | H | 4-Br | H | H | HCl (1:1) |
| 4 | B1b | 7-Cl | 3-CF₃ | H | H | HBr (1:1) |
| 480 | B1a | H | 4-S(O)₂—NH₂ | H | H | HCl (1:1) |
| 497 | B1a | H | 3-S(O)₂—NH₂ | H | H | HCl (1:1) |
| 223 | B1a | H | 3-S(O)₂—CH₃ | H | H | HCl (1:1) |
| 239 | B1a | H | 3-CH₂—OH | H | H | HCl (1:1) |
| 244 | B1a | H | 3-O—CH₃ | 4-O—CH₃ | H | HCl (1:1) |
| 254 | B1a | H | 3-CF₃ | H | H | HCl (1:1) |
| 265 | B1a | H | 4-CF₃ | H | H | HCl (1:1) |
| 291 | B1a | H | 4-N₃ | H | H | |
| 299 | B1a | H | 4-C(=O)—CH₃ | H | H | HCl (1:1) |
| 311 | B1a | H | 3-CH₃ | 4-F | H | HCl (1:1); mp. 250–252° C. (dec)* |

*= decomposition

TABLE 3

| Co. no. | Ex. no. | R¹ | Het | Physical data |
|---|---|---|---|---|
| 88 | B1b | H | 4-pyridinyl | HBr (1:1) |
| 89 | B1b | H | 2-thiazolyl | HBr (1:1) |
| 91 | B1b | H | 1H-pyrazol-3-yl | HBr (1:1); mp. 188° C. |
| 93 | B1b | H | 3-benzo[b]furanyl | HBr (1:1) |
| 94 | B1b | 4-OCH₃ | 3-benzo[b]furanyl | HBr (1:1) |
| 96 | B1b | 4-OCH₃ | 4-pyridinyl | HBr (1:1); ethanolate (1:1); mp. 250° C. |
| 97 | B1b | 4-OCH₃ | 1H-pyrazol-3-yl | HBr (1:1) |
| 98 | B1b | 4-OCH₃ | 2-thiazolyl | HBr (1:2) |
| 100 | B1b | 3-CF₃ | 3-quinolinyl | HBr (1:1); H₂O (1:1); mp. 171–173° C. (dec)* |
| 102 | B1b | 3-CF₃ | 4-pyridinyl | HBr (1:1); mp. >250° C. |
| 103 | B1b | 3-CF₃ | 2-thiazolyl | HBr (1:1); mp. 222° C. |
| 106 | B1b | 4-OCH₃ | 3-quinolinyl | HBr (1:1); H₂O (1:1) |
| 108 | B1b | 4-OCH₃ | 1H-indazol-3-yl | HBr (1:1); mp. 212° C. |
| 111 | B1b | 3-CF₃ | 1H-indazol-3-yl | HBr (1:1) |

TABLE 3-continued

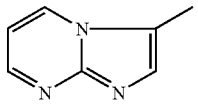

| Co. no. | Ex. no. | R¹ | Het | Physical data |
|---|---|---|---|---|
| 112 | B1b | H | 1H-indazol-3-yl | HBr (1:1); mp. 238° C. |
| 113 | B1b | 4-CH₃ | 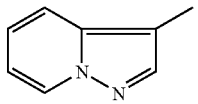 | |
| 119 | B1b | 3-CH₃ | 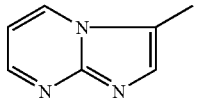 | HBr (1:1); mp. 202–204° C. (dec)* |
| 120 | B1b | 4-Br | 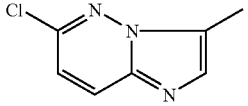 | HBr (1:1) |
| 125 | B1c | 4-OCH₃ | 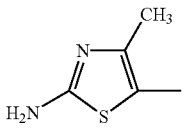 | HBr (1:1) |
| 140 | B1b | 4-CH₃ | 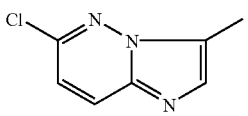 | HBr (1:2); mp. >260° C. |
| 145 | B1b | 4-OC₂H₅ | 2,4-dimethyl-5-thiazolyl | |
| 146 | B1b | 4-SO₂—NH₂ | 2-amino-4-methyl-5-thiazolyl | |
| 332 | B1c | 3-CF₃ | 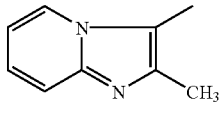 | HBr (1:1) |
| 359 | B1a | H | 4-pyridinyl | |
| 373 | B1a | 3-CH₃ | 4-pyridinyl | |
| 387 | B1a | 4-NH₂ | 4-pyridinyl | HBr (1:1) |
| 427 | B1a | 4-CH₃ | 4-pyridinyl | |
| 437 | B1a | 4-O—C₂H₅ | 4-pyridinyl | |
| 449 | B1a | 3-OH | 4-pyridinyl | |
| 511 | B1b | 3-CF₃ | 1,2-dimethyl-1H-imidazol-5-yl | HBr (1:1) |
| 512 | B1b | 3-Cl | 4-pyridinyl | HBr (1:1) |
| 513 | B1a | H | 5-chloro-2-thienyl | |
| 514 | B1a | 4-Br | 2,4-dimethyl-5-thiazolyl | |
| 515 | B1a | 3-CH₃ | 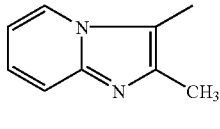 | |
| 516 | B1a | 3-OH | | |

TABLE 3-continued

| Co. no. | Ex. no. | R¹ | Het | Physical data |
|---|---|---|---|---|
| 517 | B1b | 3-CF₃ | 5-pyrimidinyl | mp 214° C. |
| 518 | B1b | 3-CF₃ | 3-furanyl | HCl (1:1); mp. 120–122° C. (dec)* |
| 519 | B1b | 3-CF₃ | 2-furanyl | HCl (1:1) |

*= decomposition

TABLE 4

| Co. no. | Ex. no. | Het | Q | Physical data |
|---|---|---|---|---|
| 130 | B1a | imidazo[1,2-a]pyridin-3-yl | 1,3-benzodioxol-5-yl | HCl (1:1) |
| 131 | B1b | imidazo[1,2-a]pyridin-2-yl | 1,3-benzodioxol-5-yl | HBr (1:1) |
| 132 | B1b | imidazo[1,2-a]pyrazin-3-yl | 3-pyridinyl | |
| 133 | B1c | pyrazolo[1,5-a]pyridin-3-yl | 3-pyridinyl | HBr (1:1); H₂O (1:1) |
| 143 | B1c | 2-methyl-imidazo[1,2-a]pyridin-3-yl | 2-pyridinyl | HBr (1:1) |
| 150 | B1b | 2-methyl-imidazo[1,2-a]pyridin-3-yl | cyclohexyl | |
| 201 | B1a | 1H-pyrrolo[2,3-b]pyridin-3-yl | 1,3-benzodioxol-5-yl | HCl (1:2) |
| 202 | B1a | 1H-pyrrolo[2,3-b]pyridin-3-yl | 1-naphthalenyl | HCl (1:2) |

TABLE 4-continued

[Structure: thiazole with Het at 4-position and NH-Q at 2-position]

| Co. no. | Ex. no. | Het | Q | Physical data |
|---|---|---|---|---|
| 237 | B1b | imidazo[1,2-a]pyrazin-3-yl | 1,3-benzodioxol-5-yl | HBr (1:1) |
| 238 | B1b | imidazo[1,2-a]pyrazin-3-yl | 1-naphthalenyl | HBr (1:1) |
| 426 | B1a | imidazo[1,5-a]pyridin-3-yl | 1-naphthalenyl | HCl (1:1) |
| 510 | B1a | imidazo[1,2-a]pyridin-2-yl | 1-naphthalenyl | HBr (1:1) |
| 218 | B1a | 1H-indol-3-yl | cyclohexyl | HCl (1:1) |
| 520 | B1a | 4-pyridinyl | 2,6-dichlorophenyl | |
| 521 | B1a | 4-pyridinyl | 2,6-dimethylphenyl | |
| 522 | B1a | 1H-pyrrolo[2,3-b]pyridin-3-yl | 3-pyridinyl | HBr (1:2) |
| 523 | B1a | 5-chloro-2-thienyl | 3-pyridinyl | HBr (1:1) |
| 524 | B1a | 2-methyl-imidazo[1,2-a]pyridin-3-yl | 2-pyridinyl | |
| 525 | B1b | 3-furanyl | 2,3-dichlorophenyl | |
| 526 | B1a | imidazo[1,2-a]pyrazin-3-yl | 6-methoxy-3-pyridinyl | mp. 210–212° C. (dec)* |
| 527 | B1a | 1,2-dimethy-1H-imidazol-5-yl | 6-chloro-3-pyridinyl | HBr (1:1); mp. 174–176° C. (dec) |

TABLE 5

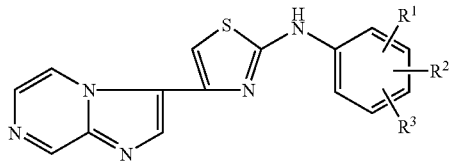

| Co. no. | Ex. no. | R¹ | R² | R³ | Physical data |
|---|---|---|---|---|---|
| 2 | B1b | 4-Cl | H | H | HBr (1:1) |
| 114 | B1b | 4-OCH₃ | H | H | HBr (1:1) |
| 115 | B1b | 3-CH₃ | H | H | HBr (1:1); H₂O (1:1) |
| 116 | B1b | 4-CH₃ | H | H | HBr (1:1); H₂O (1:1) |
| 117 | B1b | H | H | H | HBr (1:1); H₂O (1:1) |
| 118 | B1b | 3-OH | H | H | HBr (1:1) |
| 121 | B1b | 3-CF₃ | H | H | |
| 123 | B1b | 4-Br | H | H | HBr (1:1) |
| 219 | B1b | 2-Cl | 4-Cl | 5-Cl | HBr (1:1) |
| 220 | B1b | 2-OCH₃ | 4-Cl | 5-OCH₃ | HBr (1:1) |
| 221 | B1b | 2-CH₃ | 4-CH₃ | 5-CH₃ | HBr (1:1) |
| 222 | B1b | 2-CH₃ | 5-Cl | H | HBr (1:1) |
| 224 | B1b | 2-Cl | 5-Cl | H | HBr (1:1) |
| 225 | B1b | 2-OCH₃ | 5-Cl | H | HBr (1:1) |
| 226 | B1b | 2-OCH₃ | 5-CH₃ | H | HBr (1:1) |
| 227 | B1b | 2-OCH₃ | 5-OCH₃ | H | HBr (1:1) |
| 228 | B1b | 3-Cl | 5-Cl | H | HBr (1:1) |
| 229 | B1b | 3-CH₃ | 5-CH₃ | H | HBr (1:1) |
| 230 | B1b | 2-OCH₃ | 4-OCH₃ | H | HBr (1:1) |
| 231 | B1b | 3-F | 4-F | H | HBr (1:1) |
| 232 | B1b | 2-Cl | 4-Cl | H | HBr (1:1) |
| 233 | B1b | 2-CH₃ | 4-Cl | H | HBr (1:1) |
| 234 | B1b | 3-Cl | 4-Cl | H | HBr (1:1) |
| 235 | B1b | 3-CF₃ | 4-Cl | H | HBr (1:1) |
| 236 | B1b | 4-CH₃ | 3-Cl | H | HBr (1:1) |
| 240 | B1b | 2-OCH₃ | H | H | HBr (1:1) |
| 241 | B1b | 2-OH | H | H | HBr (1:1) |
| 242 | B1b | 2-Br | H | H | HBr (1:1) |
| 243 | B1b | 3-SCH₃ | H | H | HBr (1:1) |
| 245 | B1b | 3-F | H | H | HBr (1:1) |
| 246 | B1b | 3-CN | H | H | HBr (1:1) |
| 247 | B1b | 3-Cl | H | H | HBr (1:1) |
| 248 | B1b | 3-COOH | H | H | HBr (1:1) |
| 249 | B1b | 3-COOC₂H₅ | H | H | HBr (1:1) |
| 250 | B1b | 3-Br | H | H | HBr (1:1) |
| 251 | B1b | 4-OH | H | H | HBr (1:1) |
| 252 | B1b | 4-phenoxy | H | H | HBr (1:1) |
| 253 | B1b | 4-OCH₂-phenyl | H | H | HBr (1:1) |
| 255 | B1b | 4-F | H | H | HBr (1:1) |
| 256 | B1b | 4-cyclohexyl | H | H | HBr (1:1) |
| 257 | B1b | 4-COOH | H | H | HBr (1:1) |
| 258 | B1b | 4-COOC₂H₅ | H | H | HBr (1:1) |
| 259 | B1b | 4-COCH₃ | H | H | HBr (1:1) |
| 260 | B1b | 4-OC₂H₅ | H | H | HBr (1:1) |
| 261 | B1b | 4-C₂H₅ | H | H | HBr (1:1) |

TABLE 6

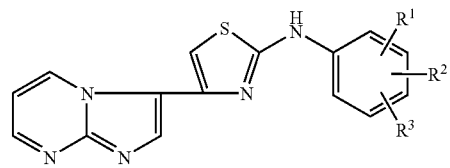

| Co. no. | Ex. no. | R¹ | R² | R³ | Physical data |
|---|---|---|---|---|---|
| 262 | B1b | 2-(2,4-dichlorophenoxy) | H | H | HBr (1:1) |
| 263 | B1b | 3-OCH₃ | 4-OCH₃ | 5-OCH₃ | HBr (1:1) |
| 264 | B1b | 2-CH₃ | 4-CH₃ | 5-CH₃ | HBr (1:1) |
| 266 | B1b | 2-F | 5-F | H | HBr (1:1) |
| 267 | B1b | 2-Cl | 5-Cl | H | HBr (1:1) |

TABLE 6-continued

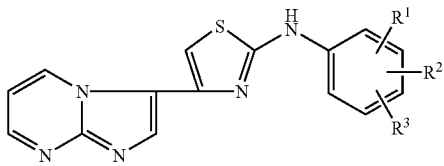

| Co. no. | Ex. no. | R¹ | R² | R³ | Physical data |
|---|---|---|---|---|---|
| 268 | B1b | 2-Cl | 5-CF₃ | H | HBr (1:1) |
| 269 | B1b | 2-OCH₃ | 5-Cl | H | HBr (1:1) |
| 270 | B1b | 2-OCH₃ | 5-CH₃ | H | HBr (1:1) |
| 271 | B1b | 2-OCH₃ | 5-OCH₃ | H | HBr (1:1) |
| 272 | B1b | 3-Cl | 5-Cl | H | HBr (1:1) |
| 273 | B1b | 2-Cl | 3-Cl | H | HBr (1:1) |
| 274 | B1b | 2-CH₃ | 3-Cl | H | HBr (1:1) |
| 275 | B1b | 3-CH₃ | 5-CH₃ | H | HBr (1:1) |
| 276 | B1b | 3-CF₃ | 5-CF₃ | H | HBr (1:1) |
| 277 | B1b | 2-OCH₃ | 4-OCH₃ | H | HBr (1:1) |
| 278 | B1b | 2-F | 4-F | H | HBr (1:1) |
| 279 | B1b | 3-F | 4-F | H | HBr (1:1) |
| 280 | B1b | 2-Cl | 4-Cl | H | HBr (1:1) |
| 281 | B1b | 2-CH₃ | 4-Cl | H | HBr (1:1) |
| 282 | B1b | 3-Cl | 4-Cl | H | HBr (1:1) |
| 283 | B1b | 3-CF₃ | 4-Cl | H | HBr (1:1) |
| 284 | B1b | 2-Br | 4-CH₃ | H | HBr (1:1) |
| 285 | B1b | 2-CH₃ | 4-CH₃ | H | HBr (1:1) |
| 286 | B1b | 3-Cl | 4-CH₃ | H | HBr (1:1) |
| 287 | B1b | 2-Cl | 4-CF₃ | H | HBr (1:1) |
| 288 | B1b | 2-CF₃ | 4-Br | H | HBr (1:1) |
| 289 | B1b | 3-Cl | 4-Br | H | HBr (1:1) |
| 292 | B1b | 2-OCH₃ | H | H | HBr (1:1) |
| 293 | B1b | 2-OH | H | H | HBr (1:1) |
| 294 | B1b | 2-Cl | H | H | HBr (1:1) |
| 295 | B1b | 2-F | H | H | HBr (1:1) |
| 296 | B1b | 2-CF₃ | H | H | HBr (1:1) |
| 297 | B1b | 3-SCH₃ | H | H | HBr (1:1) |
| 298 | B1b | 3-OH | H | H | HBr (1:1) |
| 300 | B1b | 3-F | H | H | HBr (1:1) |
| 301 | B1b | 3-CN | H | H | HBr (1:1) |
| 302 | B1b | 3-Cl | H | H | HBr (1:1) |
| 303 | B1b | 3-COOH | H | H | HBr (1:1) |
| 304 | B1b | 3-COOC₂H₅ | H | H | HBr (1:1) |
| 305 | B1b | 3-COCH₃ | H | H | HBr (1:1) |
| 306 | B1b | 3-Br | H | H | HBr (1:1) |
| 307 | B1b | 4-phenoxy | H | H | HBr (1:1) |
| 308 | B1b | 4-OC₂H₅ | H | H | HBr (1:1) |
| 309 | B1b | 4-OCF₃ | H | H | HBr (1:1) |
| 310 | B1b | 4-OCH₂-phenyl | H | H | HBr (1:1) |
| 312 | B1b | 4-F | H | H | HBr (1:1) |
| 313 | B1b | 4-cyclohexyl | H | H | HBr (1:1) |
| 314 | B1b | 4-Cl | H | H | HBr (1:1) |
| 315 | B1b | 4-C₂H₅ | H | H | HBr (1:1) |
| 316 | B1b | 4-COOH | H | H | HBr (1:1) |
| 317 | B1b | 4-COOC₂H₅ | H | H | HBr (1:1) |
| 319 | B1b | 2-SCH₃ | H | H | HBr (1:1) |
| 320 | B1b | 2-OCF₃ | H | H | HBr (1:1) |
| 321 | B1b | 2-Br | H | H | HBr (1:1) |
| 322 | B1b | 2-C₂H₅ | H | H | HBr (1:1) |
| 323 | B1b | 2-CH₃ | 3-CH₃ | H | HBr (1:1) |
| 528 | B1b | 2-F | 3-F | 4-F | HBr (1:1) |
| 529 | B1b | 2-Cl | 4-Cl | 5-Cl | HBr (1:1) |
| 530 | B1b | 2-OCH₃ | 4-Cl | 5-OCH₃ | HBr (1:1) |
| 531 | B1b | 2-CH₃ | 5-F | H | HBr (1:1) |
| 532 | B1b | 2-CH₃ | 5-Cl | H | HBr (1:1) |
| 533 | B1b | 2-O—C₂H₅ | H | H | HBr (1:1) |
| 534 | B1c | 3-CH₃ | H | H | HCl (1:1) |
| 535 | B1b | 4-CF₃ | H | H | HBr (1:1) |
| 536 | B1b | 3-CF₃ | H | H | HBr (1:1) |

TABLE 7

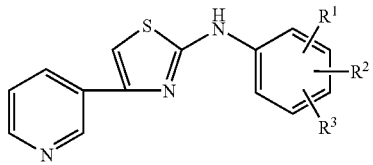

| Co. no. | Ex. no. | R¹ | R² | R³ | Physical data |
|---|---|---|---|---|---|
| 95 | B1b | 4-OCH₃ | H | H | HBr (1:2); mp. 228° C. |
| 101 | B1b | 3-CF₃ | H | H | HBr (1:1); mp. 238° C. |
| 122 | B1b | 4-Br | H | H | HBr (1:1) |
| 147 | B1b | 4-OCH₃ | H | H | |
| 148 | B1b | 3-OH | H | H | |
| 149 | B1b | 4-SO₂—NH₂ | H | H | HBr (1:1) |
| 324 | B1b | 2-(2,4-dichlorophenoxy) | H | H | HBr (1:1) |
| 325 | B1b | 3-OCH₃ | 4-OCH₃ | 5-OCH₃ | HBr (1:1) |
| 326 | B1b | 2-F | 3-F | 4-F | HBr (1:1) |
| 327 | B1b | 2-Cl | 4-Cl | 5-Cl | HBr (1:1) |
| 328 | B1b | 2-OCH₃ | 4-Cl | 5-OCH₃ | HBr (1:1) |
| 329 | B1b | 2-CH₃ | 4-CH₃ | 5-CH₃ | HBr (1:1) |
| 330 | B1b | 2-CH₃ | 5-F | H | HBr (1:1) |
| 331 | B1b | 2-CH₃ | 5-Cl | H | HBr (1:1) |
| 333 | B1b | 2-F | 5-F | H | HBr (1:1) |
| 334 | B1b | 2-Cl | 5-Cl | H | HBr (1:1) |
| 335 | B1b | 2-OCH₃ | 5-Cl | H | HBr (1:1) |
| 336 | B1b | 2-OCH₃ | 5-CH₃ | H | HBr (1:1) |
| 337 | B1b | 2-OCH₃ | 5-OCH₃ | H | HBr (1:1) |
| 338 | B1b | 3-Cl | 5-Cl | H | HBr (1:1) |
| 339 | B1b | 2-Cl | 3-Cl | H | HBr (1:1) |
| 340 | B1b | 3-Cl | 3-Cl | H | HBr (1:1) |
| 341 | B1b | 2-CH₃ | 3-CH₃ | H | HBr (1:1) |
| 342 | B1b | 3-CH₃ | 5-CH₃ | H | HBr (1:1) |
| 343 | B1b | 3-CF₃ | 5-CF₃ | H | HBr (1:1) |
| 344 | B1b | 2-OCH₃ | 4-OCH₃ | H | HBr (1:1) |
| 345 | B1b | 2-F | 4-F | H | HBr (1:1) |
| 346 | B1b | 3-F | 4-F | H | HBr (1:1) |
| 347 | B1b | 2-Cl | 4-Cl | H | HBr (1:1) |
| 348 | B1b | 2-CH₃ | 4-Cl | H | HBr (1:1) |
| 349 | B1b | 3-Cl | 4-Cl | H | HBr (1:1) |
| 350 | B1b | 3-CF₃ | 4-Cl | H | HBr (1:1) |
| 351 | B1b | 2-Br | 4-CH₃ | H | HBr (1:1) |
| 352 | B1b | 2-CH₃ | 4-CH₃ | H | HBr (1:1) |
| 353 | B1b | 3-Cl | 4-CH₃ | H | HBr (1:1) |
| 354 | B1b | 2-Cl | 4-CF₃ | H | HBr (1:1) |
| 355 | B1b | 2-CF₃ | 4-Br | H | HBr (1:1) |
| 356 | B1b | 3-Cl | 4-Br | H | HBr (1:1) |
| 360 | B1b | 2-OCH₃ | H | H | HBr (1:1) |
| 361 | B1b | 2-OH | H | H | HBr (1:1) |
| 362 | B1b | 2-Cl | H | H | HBr (1:1) |
| 363 | B1b | 2-F | H | H | HBr (1:1) |
| 364 | B1b | 2-CF₃ | H | H | HBr (1:1) |
| 365 | B1b | 2-C₂H₅ | H | H | HBr (1:1) |
| 366 | B1b | 2-OC₂H₅ | H | H | HBr (1:1) |
| 367 | B1b | 2-SCH₃ | H | H | HBr (1:1) |
| 368 | B1b | 2-CH(CH₃)₂ | H | H | HBr (1:1) |
| 369 | B1b | 2-OCF₃ | H | H | HBr (1:1) |
| 370 | B1b | 2-Br | H | H | HBr (1:1) |
| 371 | B1b | 3-SCH₃ | H | H | HBr (1:1) |
| 372 | B1b | 3-OCH₃ | H | H | HBr (1:1) |
| 374 | B1b | 3-F | H | H | HBr (1:1) |
| 375 | B1b | 3-CN | H | H | HBr (1:1) |
| 376 | B1b | 3-Cl | H | H | HBr (1:1) |
| 377 | B1b | 3-CH₃ | H | H | HBr (1:1) |
| 378 | B1b | 3-COOH | H | H | HBr (1:1) |
| 379 | B1b | 3-COOC₂H₅ | H | H | HBr (1:1) |
| 380 | B1b | 3-COCH₃ | H | H | HBr (1:1) |
| 381 | B1b | 3-Br | H | H | HBr (1:1) |
| 382 | B1b | 4-OH | H | H | HBr (1:1) |
| 383 | B1b | 4-phenoxy | H | H | HBr (1:1) |
| 384 | B1b | 4-OC₂H₅ | H | H | HBr (1:1) |
| 385 | B1b | 4-OCF₃ | H | H | HBr (1:1) |
| 386 | B1b | 4-OCH₂-phenyl | H | H | HBr (1:1) |
| 388 | B1b | 4-F | H | H | HBr (1:1) |
| 389 | B1b | 4-cyclohexyl | H | H | HBr (1:1) |
| 390 | B1b | 4-Cl | H | H | HBr (1:1) |
| 391 | B1b | 4-C₂H₅ | H | H | HBr (1:1) |
| 392 | B1b | 4-CF₃ | H | H | HBr (1:1) |
| 393 | B1b | 4-COOH | H | H | HBr (1:1) |
| 394 | B1b | 4-COOC₂H₅ | H | H | HBr (1:1) |
| 395 | B1b | 4-COCH₃ | H | H | HBr (1:1) |
| 537 | B1a | H | H | H | |
| 538 | B1b | 3-[SO₂—NH₂] | H | H | HBr (1:1) |
| 539 | B1b | 3-CH₂—OH | H | H | HBr (1:1) |
| 540 | B1b | 3-OCH₃ | 4-OCH₃ | | HBr (1:2) |
| 541 | B1b | 4-CH₃ | H | H | HBr (1:2) |
| 542 | B1b | 2-Cl | 3-Cl | H | |
| 543 | B1b | 3-CH₃ | 4-F | H | HBr (1:1); mp. 242–244° C. (dec)* |

*= decomposition

TABLE 8

| Co. no. | Ex. no. | R¹ | R² | R³ | Physical data |
|---|---|---|---|---|---|
| 216 | B1a | 4-CH₃ | H | H | HCl (1:1) |
| 49 | B1a | 3-CF₃ | H | H | HCl (1:1); mp. 246° C. |
| 50 | B1a | H | H | H | HCl (1:1); mp. 228° C. |
| 51 | B1a | 3-OCH₃ | H | H | HCl (1:1); mp. 214° C. |
| 53 | B1a | 4-Br | H | H | HCl (1:1) |
| 396 | B1a | 2-(2,4-dichlorophenoxy) | H | H | HCl (1:1) |
| 397 | B1a | 2-F | 3-F | 4-F | HCl (1:1) |
| 398 | B1a | 2-Cl | 4-Cl | 5-Cl | HCl (1:1) |
| 399 | B1a | 2-OCH₃ | 4-Cl | 5-OCH₃ | HCl (1:1) |
| 400 | B1a | 2-CH₃ | 4-CH₃ | 5-CH₃ | HCl (1:1) |
| 401 | B1a | 2-CH₃ | 5-F | H | HCl (1:1) |
| 402 | B1a | 2-CH₃ | 5-Cl | H | HCl(1.1) |
| 404 | B1a | 2-F | 5-F | H | HCl (1:1) |
| 405 | B1a | 2-Cl | 5-Cl | H | HCl (1:1) |
| 406 | B1a | 2-Cl | 5-CF₃ | H | HCl (1:1) |
| 407 | B1a | 2-OCH₃ | 5-Cl | H | HCl (1:1) |
| 408 | B1a | 2-OCH₃ | 5-OCH₃ | H | HCl (1:1) |
| 409 | B1a | 3-Cl | 5-Cl | H | HCl (1:1) |
| 410 | B1a | 2-Cl | 3-Cl | H | HCl (1:1); mp. 202–204° C. (dec)* |
| 411 | B1a | 2-CH₃ | 3-Cl | H | HCl (1:1) |
| 412 | B1a | 3-CH₃ | 5-CH₃ | H | HCl (1:1) |
| 413 | B1a | 3-CF₃ | 5-CF₃ | H | HCl (1:1) |
| 414 | B1a | 2-F | 4-F | H | HCl (1:1) |
| 415 | B1a | 3-F | 4-F | H | HCl (1:1) |
| 416 | B1a | 2-Cl | 4-Cl | H | HCl (1:1) |
| 417 | B1a | 2-CH₃ | 4-Cl | H | HCl (1:1) |
| 418 | B1a | 3-Cl | 4-Cl | H | HCl (1:1) |
| 419 | B1a | 3-CF₃ | 4-Cl | H | HCl (1:1) |
| 420 | B1a | 2-Br | 4-CH₃ | H | HCl (1:1) |
| 421 | B1a | 2-CH₃ | 4-CH₃ | H | HCl (1:1) |
| 422 | B1a | 3-Cl | 4-CH₃ | H | HCl (1:1) |
| 423 | B1a | 2-Cl | 4-CF₃ | H | HCl (1:1) |
| 424 | B1a | 2-CF₃ | 4-Br | H | HCl (1:1) |
| 425 | B1a | 3-Cl | 4-Br | H | HCl (1:1) |
| 428 | B1a | 2-OCH₃ | H | H | HCl (1:1) |
| 429 | B1a | 2-OH | H | H | HCl (1:1) |
| 430 | B1a | 2-Cl | H | H | HCl (1:1) |
| 431 | B1a | 2-F | H | H | HCl (1:1) |
| 432 | B1a | 2-CH₃ | H | H | HCl (1:1) |
| 433 | B1a | 2-OC₂H₅ | H | H | HCl (1:1) |
| 434 | B1a | 2-SCH₃ | H | H | HCl (1:1) |
| 435 | B1a | 2-OCF₃ | H | H | HCl (1:1) |
| 436 | B1a | 3-SCH₃ | H | H | HCl (1:1) |
| 438 | B1a | 3-F | H | H | HCl (1:1) |
| 439 | B1a | 3-CN | H | H | HCl (1:1) |
| 440 | B1a | 3-Cl | H | H | HCl (1:1) |
| 441 | B1a | 3-COOH | H | H | HCl (1:1) |
| 442 | B1a | 3-COOC₂H₅ | H | H | HCl (1:1) |
| 443 | B1a | 3-COCH₃ | H | H | HCl (1:1) |
| 444 | B1a | 3-Br | H | H | HCl (1:1) |
| 445 | B1a | 4-OH | H | H | HCl (1:1) |
| 446 | B1a | 4-OC₂H₅ | H | H | HCl (1:1) |
| 447 | B1a | 4-OCF₃ | H | H | HCl (1:1) |
| 448 | B1a | 4-OCH₂-phenyl | H | H | HCl (1:1) |
| 450 | B1a | 4-F | H | H | HCl (1:1) |
| 451 | B1a | 4-cyclohexyl | H | H | HCl (1:1) |
| 452 | B1a | 4-C₂H₅ | H | H | HCl (1:1) |
| 453 | B1a | 4-COOH | H | H | HCl (1:1) |
| 454 | B1a | 4-COOC₂H₅ | H | H | HCl (1:1) |
| 455 | B1a | 4-COCH₃ | H | H | HCl (1:1) |
| 456 | B1a | 3-OCH₃ | 4-OCH₃ | 5-OCH₃ | HCl (1:1) |
| 457 | B1a | 2-OCH₃ | 5-CH₃ | H | HCl (1:1) |
| 458 | B1a | 2-CH₃ | 3-CH₃ | H | HCl (1:1) |
| 459 | B1a | 2-OCH₃ | 4-OCH₃ | H | HCl (1:1) |

TABLE 8-continued

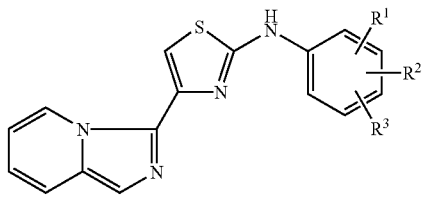

| Co. no. | Ex. no. | R¹ | R² | R³ | Physical data |
|---|---|---|---|---|---|
| 460 | B1a | 2-CF$_3$ | H | H | HCl (1:1) |
| 461 | B1a | 2-C$_2$H$_5$ | H | H | HCl (1:1) |
| 462 | B1a | 2-CH(CH$_3$)$_2$ | H | H | HCl (1:1) |
| 463 | B1a | 2-Br | H | H | HCl (1:1) |
| 464 | B1a | 4-phenoxy | H | H | HCl (1:1) |
| 544 | B1a | 4-OCH$_3$ | H | H | HCl (1:1) |
| 545 | B1a | 3-OH | H | H | HCl (1:1); H$_2$O (1:1); mp. 186° C. |

*= decomposition

TABLE 9

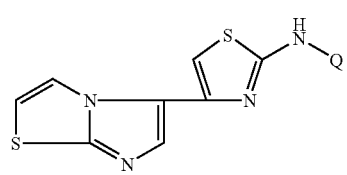

| Co. no. | Ex. no | Q | Physical data |
|---|---|---|---|
| 546 | B1a | 6-chloro-3-pyridinyl | HCl (1:1) |
| 547 | B1a | 3-pyridinyl | HCl (1:2); H$_2$O (1:1) |
| 548 | B1a | 6-methyl-3-pyridinyl | HCl (1:2) |
| 549 | B1a | 3-(trifluoromethyl)phenyl | HCl (1:1); mp. 170–172° C. (dec)* |
| 550 | B1a | 3-methylphenyl | HCl (1:1) |
| 551 | B1a | 2,3-dichlorophenyl | HCl (1:1); mp. 164–166° C. (dec)* |
| 552 | B1a | 5-benzo[b]furanyl | HCl (1:1) |
| 553 | B1a | 3-(methylthio)phenyl | HCl (1:1) |
| 554 | B1a | 3-hydroxyphenyl | HCl (1:1) |
| 555 | B1a | 3-methoxyphenyl | HCl (1:1) |
| 556 | B1a | 3-chlorophenyl | HCl (1:1) |
| 557 | B1a | 3-(ethoxycarbonyl)phenyl | HCl (1:1) |
| 558 | B1a | 3-bromophenyl | HCl (1:1) |
| 559 | B1a | 4-(methylthio)phenyl | HCl (1:1) |
| 560 | B1a | 4-hydroxyphenyl | HCl (1:1) |
| 561 | B1a | 4-methoxyphenyl | HCl (1:1) |
| 562 | B1a | 4-chlorophenyl | HCl (1:1) |
| 563 | B1a | 4-methylphenyl | HCl (1:1) |
| 564 | B1a | 4-(trifluoromethyl)phenyl | HCl (1:1) |
| 565 | B1a | 4-(ethoxycarbonyl)phenyl | HCl (1:1) |
| 566 | B1a | 4-bromophenyl | |
| 567 | B1a | 3,4,5-trimethoxyphenyl | |
| 568 | B1a | 6-(trifluoromethyl)-3-pyridinyl | HCl (1:1); mp 242° C. |
| 569 | B1a | imidazo[1,2-a]pyridin-6-yl | HCl (1:1); H$_2$O (1:3); mp 218° C. |
| 570 | B1a | 4-fluoro-3-methylphenyl | HCl (1:1) |

*= decomposition

TABLE 10

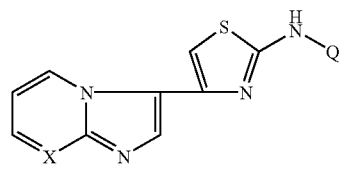

| Co. no. | Ex. no. | X | Q | Physical data |
|---|---|---|---|---|
| 126 | B1c | CH | 2-pyridinyl | HCl (1:1). |
| 127 | B1c | CH | 4-pyridinyl | HCl (1:2) |
| 128 | B1a | CH | 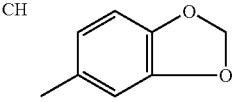 | HCl (1:1) |
| 129 | B1c | CH | 3-pyridinyl | |
| 3 | B1c | N | 3-pyridinyl | HBr (1:1) |
| 290 | B1b | N | 1-naphthalenyl | HBr (1:1) |
| 503 | B1a | CH | 1-naphthalenyl | HCl (1:1) |
| 571 | B1a | CH | 6-chloro-3-pyridinyl | HCl (1:1) |
| 572 | B1b | N | 6-chloro-3-pyridinyl | HBr (1:1) |
| 573 | B1a | CH | 6-methoxy-3-pyridinyl | |
| 574 | B1a | CH | 4-methyl-3-pyridinyl | HBr (1:1); H$_2$O (1:1) |
| 575 | B1b | N | 4-methyl-3-pyridinyl | HBr (1:1) |
| 576 | B1b | N | 6-methoxy-3-pyridinyl | |
| 577 | B1a | CH | 6-methyl-3-pyridinyl | HCl (1:2); H$_2$O (1:2) |
| 578 | B1a | CH | 6-bromo-3-pyridinyl | HCl (1:1) |
| 579 | B1a | CH | 2,3-dihydro-5-benzofuranyl | HCl (1:1); mp. 226–228° C. (dec)* |
| 580 | B1a | CH | 5-bromo-3-pyridinyl | HCl (1:1); H$_2$O (1:1) |
| 581 | B1a | CH | 5-chloro-3-pyridinyl | HCl (1:1); H$_2$O (1:1) |
| 582 | B1a | CH | 6-methyl-2-pyridinyl | HCl (1:2); H$_2$O (1:1); mp. >250° C. |
| 583 | B1a | CH | 2-methoxy-3-pyridinyl | mp. 222° C. |
| 584 | B1a | CH | 5-(trifluoromethyl)-3-pyridinyl | HCl (1:1); mp. >260° C. |
| 585 | B1a | CH | 5-methyl-2-pyridinyl | HCl (1:1); mp. 230° C. |
| 586 | B1a | CH | 6-(trifluoromethyl)-3-pyridinyl | HCl (1:1); mp. >260° C. |
| 587 | B1a | CH | 6-benzothiazolyl | HCl (1:1); mp. 210–212° C. (dec)* |
| 588 | B1a | CH | 6-hydroxy-3-pyridinyl | HBr (1:2); mp. >260° C. |
| 589 | B1a | CH | 4-methyl-2-pyridinyl | HCl (1:1); H$_2$O (1:1) |
| 590 | B1a | CH | 2,3-dihydro-1,4-benzo- | HCl (1:1); mp 220° C. |

TABLE 10-continued

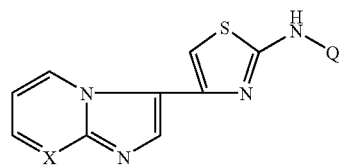

| Co. no. | Ex. no. | X | Q | Physical data |
|---|---|---|---|---|
| | | | dioxin-6-yl | |
| 591 | B1a | CH | 1H-indazole-5-yl | HCl (1:1) |
| 592 | B1a | CH | 6-(methylthio)-3-pyridinyl | HCl (1:1); mp 238° C. |
| 593 | B1a | CH | 1H-benzimidazol-5-yl | HCl (1:1); H$_2$O (1:1); mp >260° C. |
| 594 | B1a | CH | 6-ethoxy-3-pyridinyl | HCl (1:2) |
| 595 | B1a | CH | 1-methyl-1H-benzimidazol-5-yl | HCl (1:2); H$_2$O (1:2); mp 252° C. |

TABLE 10-continued

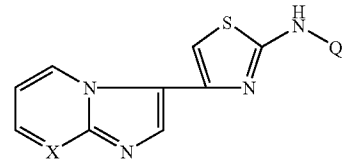

| Co. no. | Ex. no. | X | Q | Physical data |
|---|---|---|---|---|
| 596 | B1a | CH | 5-methyl-3-pyridinyl | HCl (1:1); H$_2$O (1:1); mp 212° C. |
| 597 | B1a | CH |  | HCl (1:2); mp >260° C. |

*= decomposition

TABLE 11

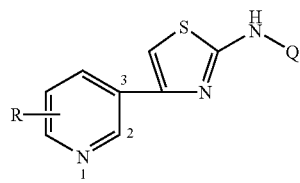

| Co. no. | Ex. no. | R | Q | Physical data |
|---|---|---|---|---|
| 357 | B1b | H | 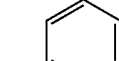 | HBr (1:1) |
| 358 | B1b | H | 1-naphthalenyl | HBr (1:1) |
| 598 | B1b | H | 3-pyridinyl | HBr (1:2); H$_2$O (1:1) |
| 599 | B1b | H | 6-chloro-3-pyridinyl | HBr (1:1) |
| 600 | B1b | H | 6-methoxy-3-pyridinyl | |
| 601 | B1b | H | 4-methyl-3-pyridinyl | HBr (1:2); H$_2$O (1:1) |
| 602 | B1b | H | 5-pyrimidinyl | HBr (1:2) |
| 603 | B1b | H | 6-bromo-3-pyridinyl | HBr (1:1); H$_2$O (1:1) |
| 604 | B1b | H | 5-chloro-3-pyridinyl | HBr (1:2) |
| 605 | B1b | H | 2,3-dihydro-5-benzofuranyl | HBr (1:1) |
| 606 | B1b | H | 5-bromo-3-pyridinyl | HBr (1:2); H$_2$O (1:1) |
| 607 | B1b | H | 6-(trifluoromethyl)-3-pyridinyl | HBr (1:2) |
| 608 | B1b | H | 6-hydroxy-3-pyridinyl | HBr (1:1) |
| 609 | B1b | H | 2-methoxy-3-pyridinyl | |
| 610 | B1b | H | 6-benzothiazolyl | HBr (1:1); H$_2$O (1:1); mp. >250° C. |
| 611 | B1b | H | 1H-indazol-5-yl | HBr (1:1); H$_2$O (1:1) |
| 612 | B1b | H | 5-(trifluoromethyl)-3-pyridinyl | HBr (1:1) |
| 613 | B1b | H | 1H-benzimidazol-5-yl | HBr (1:2); mp. >260° C. |
| 614 | B1b | H | 2,3-dihydro-1,4-benzodioxin-6-yl | HBr (1:2); mp. >250° C. |
| 615 | B1b | H | 6-ethoxy-3-pyridinyl | HBr (1:2) |
| 616 | B1b | H | 6-(methylthio)-3-pyridinyl | HBr (1:2); mp >260° C. |
| 617 | B1b | H | 6-methyl-3-pyridinyl | HBr (1:2) |
| 618 | B1b | H | 1-methyl-1H-indazol-5-yl | HBr (1:1) |
| 619 | B1b | H | 1-methyl-1H-benzimidazol-5-yl | HBr (1:2); mp 246° C. |
| 620 | B1b | H | 5-methyl-3-pyridinyl | HBr (1:2) |
| 621 | B1b | 5-bromo | 3-(trifluoromethyl)phenyl | HB (1:1) |

TABLE 11-continued

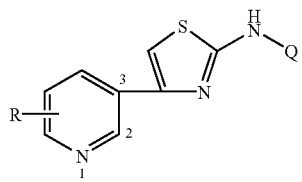

| Co. no. | Ex. no. | R | Q | Physical data |
|---|---|---|---|---|
| 622 | B1a | H | 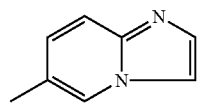 | HBr (1:2); H$_2$O (1:2); mp >260° C. |
| 623 | B1b | 6-CF$_3$ | 3-(trifluoromethyl)phenyl | HBr (1:2); mp 156° C. |
| 624 | B1b | 6-CF$_3$ | 2,3-dichlorophenyl | HBr (1:1); mp 206° C. |
| 625 | B1b | 6-CF$_3$ | 6-methyl-3-pyridinyl | HBr (1:1); mp >260° C. |
| 626 | B1d | 5-CH$_3$ | 3-(trifluoromethyl)phenyl | HBr (1:1) |
| 627 | B1d | 5-CH$_3$ | 2,3-dichlorophenyl | HBr (1:1) |
| 628 | B1b | 6-[NH—C(=O)—CH$_3$] | 3-(trifluoromethyl)phenyl | mp 248° C. |
| 629 | B1d | 6-CH$_3$ | 3-(trifluoromethyl)phenyl | HBr (1:1) |
| 630 | B1b | 6-[NH—C(=O)—CH$_3$] | 6-methyl-3-pyridinyl | HBr (1:2); H$_2$O (1:1); mp >260° C. |
| 631 | B1d | 6-CH$_3$ | 6-methyl-3-pyridinyl | HBr (1:2) |
| 632 | B1d | 5-CH$_3$ | 6-methyl-3-pyridinyl | HBr (1:2); H$_2$O (1:1) |
| 633 | B4a | 6-NH$_2$ | 6-methyl-3-pyridinyl | HBr (1:2); H$_2$O (1:2); mp >260° C. |
| 634 | B1b | 6-[NH—C(=O)—CH$_3$] | 2,3-dichlorophenyl | HBr (1:1); mp >260° C. |
| 635 | B4b | 6-NH$_2$ | 2,3-dichlorophenyl | HBr (1:2); mp 236° C. |
| 636 | B1d | 6-CH$_3$ | 2,3-dichlorophenyl | HBr (1:1); H$_2$O (1:1) |
| 637 | B5 | 6-NH$_2$ | 3-(trifluoromethyl)phenyl | HBr (1:1); H$_2$O (1:1); mp 148° C. |
| 638 | B1b | 6-[C(=O)—NH$_2$] | 3-(trifluoromethyl)phenyl | HBr (1:1); ethanolate (1:1) |
| 639 | B1b | 5-[C(=O)—NH$_2$] | 2,3-dichlorophenyl | HBr (1:1); H$_2$O (1:2); mp >260° C. |

TABLE 12

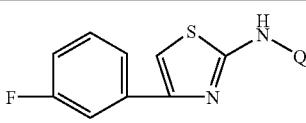

| Co. no. | Ex. no. | Q | Physical data |
|---|---|---|---|
| 640 | B1b | phenyl | |
| 641 | B1b | 4-methoxyphenyl | |
| 642 | B1b | 3-pyridinyl | |
| 643 | B1b | 3-(trifluoromethyl)phenyl | HCl (1:1) |

Table 13 lists both the experimental (column heading "Exper") and theoretical (column heading "Theor") elemental analysis values for carbon (C), hydrogen (H), nitrogen (N) and chloor (Cl) for the compounds as prepared in the experimental part hereinabove.

TABLE 13

| Co. No. | C Theor | C Exper | H Theor | H Exper | N Theor | N Exper | Cl Theor | Cl Exper |
|---|---|---|---|---|---|---|---|---|
| 18 | 61.36 | 60.55 | 4.88 | 5.00 | 11.30 | 11.09 | 9.53 | 9.20 |
| 210 | 47.11 | 46.45 | 3.46 | 3.48 | 17.17 | 16.68 | | |
| 1 | 51.92 | 51.74 | 3.59 | 3.42 | 14.25 | 14.05 | | |
| 42 | 42.26 | 42.28 | 2.66 | 2.37 | 12.32 | 12.06 | | |
| 61 | 64.26 | 63.99 | 4.79 | 4.70 | 16.65 | 16.43 | | |
| 5 | 48.25 | 49.23 | 4.3 | 4.21 | 17.58 | 17.38 | | |
| 138 | 44.61 | 44.59 | 3.74 | 3.42 | 14.86 | 14.60 | | |
| 480 | 47.11 | 47.08 | 3.46 | 3.35 | 17.17 | 17.06 | | |
| 223 | 50.18 | 49.96 | 3.72 | 3.53 | 13.77 | 13.60 | 8.96 | 9.23 |
| 239 | 56.9 | 56.97 | 4.21 | 3.96 | 15.61 | 15.32 | | |
| 291 | 57.64 | 57.10 | 3.33 | 3.02 | 29.41 | 29.11 | | |
| 299 | 58.3 | 58.36 | 4.08 | 3.94 | 15.11 | 14.94 | | |
| 93 | 54.70 | 54.49 | 3.51 | 3.30 | 7.50 | 7.39 | | |
| 113 | 62.52 | 62.06 | 4.26 | 4.19 | 22.78 | 22.63 | | |
| 125 | 43.08 | 43.79 | 2.99 | 2.63 | 15.96 | 15.63 | | |
| 140 | 36.22 | 39.32 | 3.47 | 3.69 | 12.07 | 12.62 | | |
| 511 | 42.97 | 42.78 | 3.37 | 3.16 | 13.36 | 13.09 | 0 | 0.15 |
| 517 | 52.17 | 51.94 | 2.81 | 2.61 | 17.38 | 16.90 | | |
| 518 | 48.49 | 48.08 | 2.91 | 2.66 | 8.08 | 7.94 | | |
| 132 | 57.13 | 56.27 | 3.42 | 3.27 | 28.55 | 28.37 | | |
| 133 | 45.93 | 45.55 | 3.6 | 3.22 | 17.85 | 17.40 | | |
| 150 | 65.35 | 65.46 | 6.45 | 6.45 | 17.93 | 18.08 | | |
| 218 | 61.15 | 60.49 | 6.04 | 6.24 | 12.59 | 12.16 | | |
| 602 | 34.55 | 33.85 | 2.66 | 2.98 | 16.79 | 16.28 | | |
| 525 | 50.18 | 49.67 | 2.59 | 2.64 | 9 | 8.54 | | |
| 526 | 55.54 | 54.94 | 3.73 | 3.56 | 25.91 | 24.99 | | |
| 527 | 40.38 | 39.09 | 3.39 | 3.16 | 18.11 | 17.26 | | |
| 149 | 40.68 | 41.01 | 3.17 | 2.82 | 13.56 | 13.65 | | |
| 546 | 42.17 | 42.17 | 2.45 | 2.20 | 18.91 | 18.60 | | |
| 569 | 38.71 | 39.96 | 3.9 | 3.52 | 18.06 | 18.18 | 8.05 | 16.95 |
| 579 | 58.3 | 58.25 | 4.08 | 3.75 | 15.11 | 14.93 | | |

TABLE 13-continued

| Co. No. | C Theor | C Exper | H Theor | H Exper | N Theor | N Exper | Cl Theor | Cl Exper |
|---|---|---|---|---|---|---|---|---|
| 587 | 52.91 | 52.70 | 3.13 | 3.02 | 18.15 | 18.23 | | |
| 590 | 55.89 | 55.67 | 3.91 | 3.94 | 14.48 | 14.42 | | |
| 591 | 55.36 | 54.32 | 3.55 | 3.47 | 22.78 | 22.26 | | |
| 593 | 52.78 | 54.64 | 3.91 | 4.10 | 21.72 | 22.90 | 9.42 | 9.71 |
| 605 | 51.07 | 51.01 | 3.75 | 3.46 | 11.17 | 10.94 | | |
| 623 | 34.87 | 36.06 | 2.01 | 2.08 | 7.62 | 7.75 | | |
| 628 | 53.96 | 53.23 | 3.46 | 3.17 | 14.81 | 14.50 | | |
| 638 | 44 | 43.13 | 3.69 | 3.26 | 11.4 | 11.27 | | |
| 128 | 54.77 | 54.65 | 3.51 | 3.22 | 15.03 | 14.81 | | |
| 634 | 41.76 | 41.60 | 2.85 | 2.63 | 12.18 | 11.85 | | |
| 643 | 51.28 | 51.51 | 2.96 | 2.81 | 7.47 | 7.42 | | |

C. Pharmacological Example

EXAMPLE C1

In Vitro Inhibition of TNF-α Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 $A_1$ of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 6 hours, cell-free supernatant fluids were collected by centrifugation and stored at −20° C. until tested for the presence of TNF-α.

EXAMPLE C2

In Vitro Inhibition of IL-12 Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates (Nunc, Roskilde, Denmark). Blood samples were preincubated (60 minutes at 37° C.) in a humidified 6% $CO_2$-atmosphere with 100 μl of drug solvent (final concentration 0.02% dimethylsulfoxide in RPMI 1640) or with 100 μl of an appropriate dose of test compound before being stimulated by the addition of 100 μl of lipopolysaccharide at a final concentration of 100 ng/ml. After 24 hours, cell-free supernatant fluids were collected by centrifugation and stored at −20° C. until tested for the presence of IL-12.

EXAMPLE C3

Cytokine Measurements

Cytokine protein concentrations were determined by sandwich ELISA as described in Van Wauwe et al. (1996, Inflamm Res, 45, 357–363). Murine monoclonals used as capture antibodies to human cytokines were obtained from R&D Systems (Abingdon, United Kingdom) and code named MAB210 and MAB611 for TNF-α and IL-12 respectively. Butinylated goat polyclonal antibodies used to detect human cytokines were from R&D Systems (BAF210, BAF219). Cytokine levels were calculated from standard curves using recombinant cytokines supplied by R&D Systems.

Table 14 lists the percentage inhibition of TNF-α and IL-12 production (column "% inh") at a test dose of $1 \times 10^{-6}$ and $1 \times 10^{-7}$ M for the compounds of the present invention.

TABLE 14

| Comp. No | % inhib. TNF-α $1 \times 10^{-6}$ M | % inhib. TNF-α $1 \times 10^{-7}$ M | % inhib. IL-12 (p40) $1 \times 10^{-6}$ M | % inhib. IL-12 (p40) $1 \times 10^{-7}$ M |
|---|---|---|---|---|
| 9 | 37 | 39 | 49 | 53 |
| 140 | 46 | 44 | 56 | 63 |
| 74 | 56 | 48 | 70 | 67 |
| 81 | 51 | 47 | 65 | 67 |
| 82 | 53 | 51 | 73 | 68 |
| 100 | 43 | 41 | 53 | 51 |
| 101 | 54 | 53 | 62 | 65 |
| 31 | 55 | 49 | 66 | 68 |
| 39 | 53 | 59 | 64 | 71 |
| 476 | 58 | 53 | 75 | 71 |
| 45 | 49 | 48 | 64 | 65 |
| 166 | 48 | 37 | 62 | 55 |
| 410 | 39 | 43 | 53 | 58 |
| 115 | 58 | 53 | 75 | 67 |
| 119 | 49 | 49 | 62 | 62 |
| 286 | 50 | 48 | 60 | 63 |
| 573 | 53 | 45 | 67 | 61 |
| 526 | 45 | 45 | 66 | 69 |
| 577 | 50 | 49 | 77 | 71 |
| 527 | 37 | 43 | 61 | 66 |
| 549 | 50 | 47 | 74 | 71 |
| 551 | 44 | 40 | 71 | 71 |
| 579 | 49 | 50 | 72 | 75 |
| 584 | 53 | 49 | 75 | 68 |
| 587 | 56 | 56 | 79 | 75 |
| 517 | 61 | 57 | 74 | 68 |
| 643 | 64 | 59 | 75 | 72 |
| 518 | 38 | 44 | 62 | 59 |
| 466 | 57 | 49 | 95 | 86 |
| 509 | 46 | 54 | 64 | 68 |

What is claimed is:

1. A method of inhibiting, suppressing, or antagonizing the production or activity of TNF-α (Tumor Necrosis Factor-alpha) or IL-12 (Interleukin 12) in a warm-blooded animal in need thereof comprising administering to the animal a therapeutically effective amount of a compound of the formula

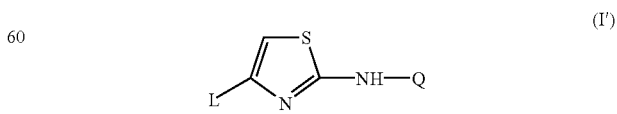

(I')

a N-oxide, a pharmaceutically acceptable addition salt, a quaternary amine and a stereochemically isomeric form thereof, wherein
- Q is phenyl, or naphthyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyl-S(=O)$_n$— or $R^1$HN—S(=O)$_n$—;
- n is an integer with value 1 or 2;
- $R^1$ represents hydrogen, or a radical of formula

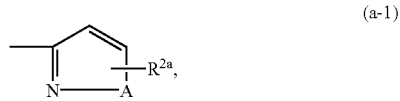

(a-1)

with A being O, S or a bivalent radical of formula —$CR^{2a}$=N— with $CR^{2a}$ attached to N of formula (a-1); and $R^2$a being hydrogen, $C_{1-6}$alkyl or $C_{1-6}$alkyloxy;

L is imidazopyridyl, optionally be substituted with up to 6 substituents, said substituents each independently being selected from halo, hydroxy, amino, cyano, carboxyl, mono-or di($C_{1-4}$alkyl)amino, $C_{1-6}$alkyl, $C_{1-6}$alkyl substituted with hydroxy or $C_{1-4}$alkyloxy or amino or mono-or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono-or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—; and aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, and mono- or di-($C_{1-6}$alkyl)amino.

2. The method of claim 1 wherein L is substituted with up to 6 substituents, said substituents each independently being selected from halo, hydroxy, amino, and mono- or di-($C_{1-4}$alkyl)amino, $C_{1-6}$alkyl, polyhalo$C_{1-6}$alkyl or $C_{1-6}$alkyloxy; and wherein aryl is phenyl, optionally substituted with up to five substituents each independently selected from halo, hydroxy, $C_{1-6}$alkyl, $C_{1-6}$alkyloxy, $C_{1-6}$alkylthio, cyano, nitro, amino, and mono- or di-$C_{1-6}$alkyl)amino.

3. A method of treating inflammatory disease mediated by TNF-α (Tumor Necrosis Factor-alpha) or IL-12 (Interleukin 12) in a warm-blooded animal in need thereof comprising administering to the animal a therapeutically effective amount of a compound of the formula

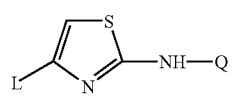

(I')

a N-oxide, a pharmaceutically acceptable addition salt, a quaternary amine and a stereochemically isomeric form thereof, wherein
- Q is phenyl, or naphthyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyk-S(=O)$_n$— or $R^1$HN—S(=O)$_n$—;
- n is an integer with value 1 or 2;
- $R^1$ represents hydrogen, or a radical of formula

(a-1)

with A being O, S or a bivalent radical of formula —$CR^{2a}$=N— with $CR^{2a}$ attached to N of formula (a-1); and $R^2$ being hydrogen, $C_{1-6}$alkyl or $C_{1-6}$alkyloxy;

L is imidazopyridyl, optionally be substituted with up to 6 substituents, said substituents each independently being selected from halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—; and aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, and mono- or di-($C_{1-6}$alkyl)amino.

4. The method of claim 3 wherein L is substituted with up to 6 substituents, said substituents each independently being selected from halo, hydroxy, amino, and mono- or di-($C_{1-4}$alkyl)amino, $C_{1-6}$alkyl, polyhalo$C_{1-6}$alkyl or $C_{1-6}$alkyloxy; and wherein aryl is phenyl, optionally substituted with up to five substituents each independently selected from halo, hydroxy, $C_{1-6}$alkyl, $C_{1-6}$alkyloxy, $C_{1-6}$alkylthio, cyano, nitro, amino, and mono- or di-$C_{1-6}$alkyl)amino.

5. The method of claim 1 wherein the inflammatory disease is rheumatoid arthritis, Crohn's disease, irritable bowel disease, or colitis.

6. A method of treating auto-immune diseases mediated by TNF-α (Tumor Necrosis Factor-alpha) or IL-12 (Interleukin 12) in a warm-blooded animal in need thereof comprising administering to the animal a therapeutically effective amount of a compound of the formula

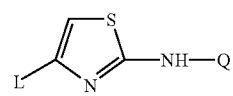

(I')

a N-oxide, a pharmaceutically acceptable addition salt, a quaternary amine and a stereochemically isomeric form thereof, wherein Q is phenyl, or naphthyl, each of said rings optionally being substituted with up to three substituents each independently selected from halo; hydroxy; cyano; carboxy; azido; amino; mono- or di($C_{1-6}$alkyl)amino; $C_{1-6}$alkyl; $C_{2-6}$alkenyl; $C_{2-6}$alkynyl; $C_{3-6}$cycloalkyl; $C_{1-6}$alkyl substituted with hydroxy, $C_{1-6}$alkyloxy, amino, mono- or di($C_{1-4}$alkyl)amino; $C_{1-6}$alkyloxy; $C_{1-6}$alkylthio; $C_{1-6}$alkylcarbonyl; $C_{1-6}$alkyloxycarbonyl; aryl$C_{1-6}$alkyloxy; aryloxy; polyhalo$C_{1-6}$alkyl; polyhalo-$C_{1-6}$alkyloxy; polyhalo$C_{1-6}$alkylcarbonyl; $C_{1-4}$alkyl-S(=O)$_n$— or $R^1$HN—S(=O)$_n$—;

n is an integer with value 1 or 2;

$R^1$ represents hydrogen, or a radical of formula

(a-1)

with A being O, S or a bivalent radical of formula —$CR^{2a}$=N— with $CR^{2a}$ attached to N of formula (a-1); and $R^{2a}$ being hydrogen, $C_{1-6}$alkyl or $C_{1-6}$alkyloxy;

L is imidazopyridyl, optionally be substituted with up to 6 substituents, said substituents each independently being selected from halo, hydroxy, amino, cyano, carboxyl, mono- or di($C_{1-4}$alkyl)amino, $C_{1-6}$alkyl, $C_{1-6}$alkyl substituted with hydroxy or $C_{1-4}$alkyloxy or amino or mono- or di($C_{1-4}$alkyl)amino, polyhalo$C_{1-6}$alkyl, $C_{1-6}$alkyloxy, $C_{1-6}$alkyloxycarbonyl, $C_{1-6}$alkylcarbonyloxy, aminocarbonyl, mono- or di($C_{1-6}$alkyl)aminocarbonyl, $C_{1-6}$alkyl-C(=O)—NH—, $C_{1-6}$alkyloxy-C(=O)—NH—, $H_2N$—C(=O)—NH— or mono- or di($C_{1-4}$alkyl)amino-C(=O)—NH—; and aryl is phenyl, optionally substituted with up to five substituents each independently selected from halo, hydroxy, $C_{1-6}$alkyl, polyhalo$C_{1-6}$alkyl, $C_{1-6}$alkyloxy, $C_{1-6}$alkylthio, cyano, nitro, amino, and mono- or di-($C_{1-6}$alkyl)amino.

7. The method of claim 6 wherein L is substituted with up to 6 substituents, said substituents each independently being selected from halo, hydroxy, amino, and mono- or di-($C_{1-4}$alkyl)amino, $C_{1-6}$alkyl, polyhalo$C_{1-6}$alkyl or $C_{1-6}$alkyloxy; and wherein aryl is phenyl, optionally substituted with up to five substituents each independently selected from halo, hydroxy, $C_{1-6}$alkyl, $C_{1-6}$alkyloxy, $C_{1-6}$alkylthio, cyano, nitro, amino, and mono- or di-$C_{1-6}$alkyl)amino.

* * * * *